US006358706B1

(12) United States Patent
Dubin et al.

(10) Patent No.: US 6,358,706 B1
(45) Date of Patent: Mar. 19, 2002

(54) DNA ENCODING HUMAN ALPHA1G-C T-TYPE CALCIUM CHANNEL

(75) Inventors: Adrienne E. Dubin; Jose E. Galindo; Jayashree Pyati; Jessica Y. Zhu; Mark G. Erlander, all of San Diego, CA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/426,998

(22) Filed: Oct. 26, 1999

(51) Int. Cl.[7] .......................... C12N 5/10; C12N 15/12; C12N 15/64; C07K 14/705

(52) U.S. Cl. .................... 435/69.1; 536/23.1; 536/23.5; 530/350; 435/71.1; 435/71.2; 435/471; 435/325; 435/252.3; 435/254.11; 435/320.1

(58) Field of Search ............................... 536/23.1, 23.5; 530/350; 435/69.1, 71.1, 71.2, 471, 325, 252.3, 254.11, 320.1

(56) References Cited

FOREIGN PATENT DOCUMENTS

WO          WO 99/28342          6/1999

OTHER PUBLICATIONS

Rieger et al. (1976) Clonary of Genetics & Cylogenetics. Springer–Verlag, pp. 16–19.*
Arnoult, Christophe; Cardullo, Richard A.; Lemos, Jose R.; Florman, Harvey M. Activation of mouse sperm T–type $Ca^{2+}$ channels by adhesion to the egg zona pellucida. Proc. Natl. Acad. Sci. USA–vol. 93, pp. 13004–13009, Nov. 1996.
Xu, Xiaoping; Best, Philip M. Increase in T–type calcium current in atrial myocytes from adult rats with growth hormone–secreting tumors. Proc. Natl. Acad. Sci. USA–vol. 87, pp. 4655–4659, Jun. 1990.
Formenti, Alessandro; Arrigoni, Eldo; Mancia, Mauro. Two distinct modulatory effects on calcium channels in adult rat sensory neurons. Biophys. J.—Biophysical Society, vol. 64, 1029–1037. Apr. 1993.
Heine, Martin; Wicher, Dieter. $Ca^{2+}$ resting current and $Ca^{2+}$ –induced $Ca^{2+}$ release in insect neurosecretory neurons. NeuroReport 9, 3309–3314, (1998).
Katz, A.M. T–type calcium channels may provide a unique target for cardiovascular therapy. European Heart Journal 1, (Supplement H), H18–H23, (1999).
Sen, Luyi, Smith, Thomas W. T–Type Ca $^{2+}$ Channels Are Abnormal in Genetically Determined Cardiomyopathic Hamster Hearts. Harvard Medical School, Department of Medicine, Cardiovascular Div. 1994.
Wang, Zheng; Estacion, Mark; Mordan, Lawrence J. $Ca^{2+}$ influx via T–type channels modulates PDGF–induced replication of mouse fibroblasts. The American Physiological Society, 0363–6143/93.

Todorovic, Slobodan M.; Lingle, Christorpher J. Pharmacological Properties of T–Type $Ca^{2+}$ Current in Adult Rat Sensory Neurons: Effects of Anticonvulsant and Anesthetic Agents. The American Physiological Society, 0022–3077/98.
Lalevee, Nathalie; Pluciennik, Frederique; Joffre, Michel. Voltage–Dependent Calcium Current with Properties of T–Type Current in Sertoli Cells for Immature Rat Testis in Primary Cultures. Biology of Reproduction 56, 680–687 (1997).
Ahnert–Hilger, Gudrun; Stadtbaumer, Adele; Strubing, Carsten; Scherubl, Hans; Schultz, Gunter; Riecken, Ernst–Otto; Wiedenmann, Bertram. Y–Aminobutyric Acid Secretion From Pancreatic Neuroendocrine Cells. Gastroenterology; 110:1595–1604, 1996.
Arnoult, Christophe; Lemos, Jose' R.; Florman, Harvey M. Voltage–dependent modulation of T–type calcium channels by protein tyrosine phosphorylation. The EMBO Journal, vol. 16 No. 7 pp. 1593–1599, 1997.
Avery, Robert B.; Johnston, Daniel. Multiple Channel Types Contribute to the Low–Voltage–Activated Calcium Current in Hippocampal CA3 Pyramidal Neurons. The Journal of Neuroscience, 16(18) :5567–5582, Sep. 15, 1996.
Cardenas, C.G.; Del Mar, L.P.; Scroggs, R.S. Variation in Serotonergic Inhibition of Calcium Channel Currents in Four Types of Rat Sensory Neurons Differentiated by Membrane Properties. Journal of Neurophysiology, vol. 74, No. 5, Nov. 1995.
Coulter, Douglas A.; Huguenard, John R.; Prince, David A. Specific petit mal anticonvulsants reduce calcium currents in thalamic neurons. Neuroscience Letters 98 (1989) 74–78.
Coulter, Douglas A., PhD; Huguenard, John R. PhD; Prince, David A. MD. Characterization of Ethosuximide Reduction of Low–Threshold Calcium Current in Thalamic Neurons. The American Neurological Association, 1989.
Enyeart, John J.; Mlinar, Boris; Enyeart, Judith A. T–Type $Ca^{2+}$ Channels Are Required for Adrenocorticotropin–Stimulated Cortisol Production by Bovine Adrenal Zona Fasciculate Cells. Molecular Endorcrinology, 0888–8809/93/1031–1040.
Huguenard, J.R.; Low–Threshold Calcium Currents In Central Nervous System Neurons. Annu. Rev. Physiol., 58:329–48, 1996.
Kirkup, A.J.; Edwards, G.; Weston, A.H. Investigation of the effects of 5–nitro–2–(3–phenylpropylamino)–benzoic acid (NPPB) on membrane currents in rat portal vein. British Journal of Pharmacololgy, 117, 175–183, (1996).
Klugbauer, Norbert; Marais, Else; Lacinova', Lubica; Hofmann, Franz. A T–type calcium channel from mouse brain. Pflugers Arch—Eur J Physiol, 437:710–715, (1999).

(List continued on next page.)

*Primary Examiner*—Prema Mertz
(74) *Attorney, Agent, or Firm*—John W. Wallan, III

(57) ABSTRACT

A DNA molecule encoding a novel isoform of the human T-type low voltage activated calcium channel (alpha1G-c) has been cloned and characterized. The biological and structural properties of this protein is disclosed, as is the amino acid and nucleotide sequence.

7 Claims, 9 Drawing Sheets-

OTHER PUBLICATIONS

Kostyuk, P.G.; Molokanova, E.A.; Pronchuk, N.F.; Savchenko, A.N.; Verkhratsky, A.N. Differenct Action Of Ethosuximide on Low– And High–Threshold Calcium Currents in Rat Sensory Neurons. Neuroscience, vol. 51, No. 4, pp. 755–758, 1992.

Lambert, Regis C.; Maulet, Yves; Mouton, Jerome; Beattie, Ruth; Volsen, Steve; De Waard, Michel; Feltz, Anne. T–Type $CA^{2+}$ Current Properties Are Not Modified by $Ca^{2+}$ Channel B Subunit Depletion in Nodosus Ganglion Neurons. The Journal of Neuroscience, 17(17):6621–6628, Sep. 1, 1997.

McCormick, David A.; Bal, Thierry. Sleep and Arousal: Thalamocortical Mechanisms. Annu. Rev. Neurosci. 1997.20:185–215.

Miller, Richard J. Multiple Calcium Channels and Neuronal Function. Science, vol. 235.

Perez–Reyes, Edward. Molecular Characterization of a Novel Family of Low Voltage–Activated, T–Type, Calcium Channels. Journal of Bioenergetics and Biomembranes, vol. 30, No. 4, 1998.

Perez–Reyes, Edward; Cribbs, Leanne L.; Daud, Asif; Lacerda, Antonio E.; Barclay, Jane; Williamson, Magali P.; Fox, Margaret; Rees, Michele; Lee, Jung–Ha. Molecular characterization of a neuronal low–voltage–activated T–type calcium channel. Nature, vol. 391, Feb. 26, 1998.

Perez–Reyes, Edward; Schneider, Toni. Molecular biology of calcium channels. Kidney International, vol. 48, pp. 1111–1124, (1995).

Randall, A.D.; Tsien, R.W. Contrasting Biophysical and Pharmacological Properties of T–type and R–type Calcium Channels. Neuropharmacology, vol. 36, No. 7, pp. 879–893, 1997.

Ertel, Sylvie I.; Ertel, Eric A., Clozel, Jean–Paul. T–Type $Ca^{2+}$ Channels and Pharmacological Blockade; Potential Pathophysiological Relevance. Cardiovascular Drugs and Therapy, 0363–6143/93.

Talley, Edmund M.; Cribbs, Leanne L.; Lee, Jung–Ha; Daud, Asiff; Perez–Reyes, Edward; Bayliss, Douglas A. Differential Distribution of Three Members of a Gene Family Encoding Low Voltage–Activated (T–Type) Calcium Channels. Journal of Neuroscience, 19(6):1895–1911,Mar. 15, 1999.

Tsakiridou, Evdoxia; Bertollini, Laura; de Curtis, Marco; Avanzini, Giuliano; Pape, Hans–Christian. Selective Increase in T–Type Calcium Conductance of Reticular Thalamic Neurons in a Rat Model of Absense Epilepsy. The Journal of Neuroscience, 15(4): 3110–3117, Apr. 1995.

Williams, Mark E.; Feldman, Daniel H.; McCue, Ann F.; Brenner, Robert; Velicelebi, Gonul; Ellis, Steven B.; Harpold, Michael M. Structure and Functional Expression of $a_1$, $a_2$, and B Subunits of a Novel Human Neuronal Calcium Channel Subtype. Neuron, vol. 8, 71–84, Jan., 1992.

William, Mark E.; Washburn Mark S.; Hans, Michael; Urrutia, Arturo; Brust, Paul F.; Prodanovich, Patricia; Harpold, Michael M.; Stauderman, Kenneth A. Structure and Functional Characterization of a Novel Human Low–Voltage Activated Calcium Channel. Journal of Neurochemistry, 1999.

Zamponi, G.W.; Bourinet, E. Snutch, T.P. Nickel Block of a Family of Neuronal Calcium Channels: Subtype– and Subunit–Dependent Action at Multiple Sites. The Journal of Membrane Biology, 151, 77–90 (1996).

Rousseau MD, PhD, FACC, Michel F.; Hyashida MD, Wataru, van Eyll, MS, Christian; Hess MD, Otto M.; Benedict MD. DPhil, FACC, Claude R.; Ahn, Sylvie, Chapelle MD, Frederic; Kobrin MD, Isaac; Pouleur MD, PhD, FACC, Hubert. Hemodynamica and Cardiac Effects of the Selective T–Type and L–Type Calcium Channel Blocking Agent Mibefradil in Patients With Varying Degrees of Left Ventricular Systolic Dysfunction. JACC vol. 28, No. 4, Oct. 1996:972–9.

Perez–Reyes, Edward; Cribbs, Leanne L.; Daud, Asif; Lacerda; Antonio E.; Barclay, Jane; Williamson, Magli P.; Fox, Margaret; Rees, Michele; Lee, Jung–Ha. Molecular characterization of a neuronal low–voltage–activated T–type calcium channel. Nature. Feb. 26, 1998, vol. 391, pp. 896–900.

* cited by examiner

FIG. 1A

SEQ.ID.NO.3. Human calcium channel alpha1G-c sequence of the coding sequence (6822 bp includes the TGA).

```
ATGGACGAGGAGGAGGATGGAGCGGGCGCCGAGGAGTCGGGACAGCCCCGGAGCTTCAT
GCGGCTCAACGACCTGTCGGGGGCCGGGGGCCGGCCGGGGCCGGGGTCAGCAGAAAAGG
ACCCGGGCAGCGCGGACTCCGAGGCGGAGGGGCTGCCGTACCCGGCGCTGGCCCCGGTG
GTTTTCTTCTACTTGAGCCAGGACAGCCGCCCGCGGAGCTGGTGTCTCCGCACGGTCTG
TAACCCCTGGTTTGAGCGCATCAGCATGTTGGTCATCCTTCTCAACTGCGTGACCCTGG
GCATGTTCCGGCCATGCGAGGACATCGCCTGTGACTCCCAGCGCTGCCGGATCCTGCAG
GCCTTTGATGACTTCATCTTTGCCTTCTTTGCCGTGGAGATGGTGGTGAAGATGGTGGC
CTTGGGCATCTTTGGGAAAAAGTGTTACCTGGGAGACACTTGGAACCGGCTTGACTTTT
TCATCGTCATCGCAGGGATGCTGGAGTACTCGCTGGACCTGCAGAACGTCAGCTTCTCA
GCTGTCAGGACAGTCCGTGTGCTGCGACCGCTCAGGGCCATTAACCGGGTGCCCAGCAT
GCGCATCCTTGTCACGTTGCTGCTGGATACGCTGCCCATGCTGGGCAACGTCCTGCTGC
TCTGCTTCTTCGTCTTCTTCATCTTCGGCATCGTCGGCGTCCAGCTGTGGGCAGGGCTG
CTTCGGAACCGATGCTTCCTACCTGAGAATTTCAGCCTCCCCCTGAGCGTGGACCTGGA
GCGCTATTACCAGACAGAGAACGAGGATGAGAGCCCCTTCATCTGCTCCCAGCCACGCG
AGAACGGCATGCGGTCCTGCAGAAGCGTGCCCACGCTGCGCGGGGACGGGGGCGGTGGC
CCACCTTGCGGTCTGGACTATGAGGCCTACAACAGCTCCAGCAACACCACCTGTGTCAA
CTGGAACCAGTACTACACCAACTGCTCAGCGGGGAGCACAACCCCTTCAAGGGCGCCA
TCAACTTTGACAACATTGGCTATGCCTGGATCGCCATCTTCCAGGTCATCACGCTGGAG
GGCTGGGTCGACATCATGTACTTTGTGATGGATGCTCATTCCTTCTACAATTTCATCTA
CTTCATCCTCCTCATCATCGTGGGCTCCTTCTTCATGATCAACCTGTGCCTGGTGGTGA
TTGCCACGCAGTTCTCAGAGACCAAGCAGCGGGAAAGCCAGCTGATGCGGGAGCAGCGT
GTGCGGTTCCTGTCCAACGCCAGCACCCTGGCTAGCTTCTCTGAGCCCGGCAGCTGCTA
TGAGGAGCTGCTCAAGTACCTGGTGTACATCCTTCGTAAGGCAGCCCGCAGGCTGGCTC
AGGTCTCTCGGGCAGCAGGTGTGCGGGTTGGGCTGCTCAGCAGCCCAGCACCCCTCGGG
GGCCAGGAGACCCAGCCCAGCAGCAGCTGCTCTCGCTCCCACCGCCGCCTATCCGTCCA
CCACCTGGTGCACCACCACCACCACCATCACCACCACTACCACCTGGGCAATGGGACGC
TCAGGGCCCCCGGGCCAGCCCGGAGATCCAGGACAGGGATGCCAATGGGTCCCGCAGG
CTCATGCTGCCACCACCCTCGACGCCTGCCCTCTCCGGGGCCCCCCCTGGTGGCGCAGA
GTCTGTGCACAGCTTCTACCATGCCGACTGCCACTTAGAGCCAGTCCGCTGCCAGGCGC
CCCCTCCCAGGTCCCCATCTGAGGCATCCGGCAGGACTGTGGGCAGCGGGAAGGTGTAT
CCCACCGTGCACACCAGCCCTCCACCGGAGACGCTGAAGGAGAAGGCACTAGTAGAGGT
GGCTGCCAGCTCTGGGCCCCCAACCCTCACCAGCCTCAACATCCCACCCGGGCCCTACA
GCTCCATGCACAAGCTGCTGGAGACACAGAGTACAGGTGCCTGCCAAAGCTCTTGCAAG
ATCTCCAGCCCTTGCTTGAAAGCAGACAGTGGAGCCTGTGGTCCAGACAGCTGCCCCTA
CTGTGCCCGGGCCGGGGCAGGGGAGGTGGAGCTCGCCGACCGTGAAATGCCTGACTCAG
ACAGCGAGGCAGTTTATGAGTTCACACAGGATGCCCAGCACAGCGACCTCCGGGACCCC
CACAGCCGGCGGCAACGGAGCCTGGGCCCAGATGCAGAGCCCAGCTCTGTGCTGGCCTT
CTGGAGGCTAATCTGTGACACCTTCCGAAAGATTGTGGACAGCAAGTACTTTGGCCGGG
GAATCATGATCGCCATCCTGGTCAACACACTCAGCATGGGCATCGAATACCACGAGCAG
CCCGAGGAGCTTACCAACGCCCTAGAAATCAGCAACATCGTCTTCACCAGCCTCTTTGC
CCTGGAGATGCTGCTGAAGCTGCTTGTGTATGGTCCCTTTGGCTACATCAAGAATCCCT
ACAACATCTTCGATGGTGTCATTGTGGTCATCAGCGTGTGGGAGATCGTGGGCCAGCAG
GGGGCGGCCTGTCGGTGCTGCGGACCTTCCGCCTGATGCGTGTGCTGAAGCTGGTGCG
CTTCCTGCCGGCGCTGCAGCGGCAGCTGGTGGTGCTCATGAAGACCATGGACAACGTGG
CCACCTTCTGCATGCTGCTTATGCTCTTCATCTTCATCTTCAGCATCCTGGGCATGCAT
CTCTTCGGCTGCAAGTTTGCCTCTGAGCGGGATGGGGACACCCTGCCAGACCGGAAGAA
TTTTGACTCCTTGCTCTGGGCCATCGTCACTGTCTTTCAGATCCTGAC
```

FIG. 1B

```
CCAGGAGGACTGGAACAAAGTCCTCTACAATGGTATGGCCTCCACGTCGTCCTGGGCGG
CCCTTTATTTCATTGCCCTCATGACCTTCGGCAACTACGTGCTCTTCAATTTGCTGGTC
GCCATTCTGGTGGAGGGCTTCCAGGCGGAGGAAATCAGCAAACGGGAAGATGCGAGTGG
ACAGTTAAGCTGTATTCAGCTGCCTGTCGACTCCCAGGGGGGAGATGCCAACAAGTCCG
AATCAGAGCCCGATTTCTTCTCACCCAGCCTGGATGGTGATGGGGACAGGAAGAAGTGC
TTGGCCTTGGTGTCCCTGGGAGAGCACCCGGAGCTGCGGAAGAGCCTGCTGCCGCCTCT
CATCATCCACACGGCCGCCACACCCATGTCGCTGCCCAAGAGCACCAGCACGGGCCTGG
GCGAGGCGCTGGGCCCTGCGTCGCGCCGCACCAGCAGCAGCGGGTCGGCAGAGCCTGGG
GCGGCCCACGAGATGAAGTCACCGCCCAGCGCCCGCAGCTCTCCGCACAGCCCCTGGAG
CGCTGCAAGCAGCTGGACCAGCAGGCGCTCCAGCCGGAACAGCCTCGGCCGTGCACCCA
GCCTGAAGCGGAGAAGCCCAAGTGGAGAGCGGCGGTCCCTGTTGTCGGGAGAAGGCCAG
GAGAGCCAGGATGAAGAGGAGAGCTCAGAAGAGGAGCGGGCCAGCCCTGCGGGCAGTGA
CCATCGCCACAGGGGGTCCCTGGAGCGGGAGGCCAAGAGTTCCTTTGACCTGCCAGACA
CACTGCAGGTGCCAGGGCTGCATCGCACTGCCAGTGGCCGAGGGTCTGCTTCTGAGCAC
CAGGACTGCAATGGCAAGTCGGCTTCAGGGCGCCTGGCCCGGGCCCTGCGGCCTGATGA
CCCCCCACTGGATGGGGATGACGCCGATGACGAGGGCAACCTGAGCAAAGGGGAACGGG
TCCGCGCGTGGATCCGAGCCCGACTCCCTGCCTGCTGCCTCGAGCGAGACTCCTGGTCA
GCCTACATCTTCCCTCCTCAGTCCAGGTTCCGCCTCCTGTGTCACCGGATCATCACCCA
CAAGATGTTCGACCACGTGGTCCTTGTCATCATCTTCCTTAACTGCATCACCATCGCCA
TGGAGCGCCCCAAAATTGACCCCACAGCGCTGAACGCATCTTCCTGACCCTCTCCAAT
TACATCTTCACCGCAGTCTTTCTGGCTGAAATGACAGTGAAGGTGGTGGCACTGGGCTG
GTGCTTCGGGGAGCAGGCGTACCTGCGGAGCAGTTGGAACGTGCTGGACGGGCTGTTGG
TGCTCATCTCCGTCATCGACATTCTGGTGTCCATGGTCTCTGACAGCGGCACCAAGATC
CTGGGCATGCTGAGGGTGCTGCGGCTGCTGCGGACCCTGCGCCCGCTCAGGGTGATCAG
CCGGGCGCAGGGGCTGAAGCTGGTGGTGGAGACGCTGATGTCCTCACTGAAACCCATCG
GCAACATTGTAGTCATCTGCTGTGCCTTCTTCATCATTTTCGGCATCTTGGGGGTGCAG
CTCTTCAAAGGGAAGTTTTTCGTGTGCCAGGGCGAGGATACCAGGAACATCACCAATAA
ATCGGACTGTGCCGAGGCCAGTTACCGGTGGGTCCGGCACAAGTACAACTTTGACAACC
TTGGCCAGGCCCTGATGTCCCTGTTCGTTTTGGCCTCCAAGGATGGTTGGGTGGACATC
ATGTACGATGGGCTGGATGCTGTGGGCGTGGACCAGCAGCCCATCATGAACCACAACCC
CTGGATGCTGCTGTACTTCATCTCGTTCCTGCTCATTGTGGCCTTCTTTGTCCTGAACA
TGTTTGTGGGTGTGGTGGTGGAGAACTTCCACAAGTGTCGGCAGCACCAGGAGGAAGAG
GAGGCCCGGCGGCGGGAGGAGAAGCGCCTACGAAGACTGGAGAAAAAGAGAAGGAGTAA
GGAGAAGCAGATGGCTGAAGCCCAGTGCAAACCTTACTACTCCGACTACTCCCGCTTCC
GGCTCCTCGTCCACCACTTGTGCACCAGCCACTACCTGGACCTCTTCATCACAGGTGTC
ATCGGGCTGAACGTGGTCACCATGGCCATGGAGCACTACCAGCAGCCCCAGATTCTGGA
TGAGGCTCTGAAGATCTGCAACTACATCTTCACTGTCATCTTTGTCTTGGAGTCAGTTT
TCAAACTTGTGGCCTTTGGTTTCCGTCGGTTCTTCCAGGACAGGTGGAACCAGCTGGAC
CTGGCCATTGTGCTGCTGTCCATCATGGGCATCACGCTGGAGGAAATCGAGGTCAACGC
CTCGCTGCCCATCAACCCCACCATCATCCGCATCATGAGGGTGCTGCGCATTGCCCGAG
TGCTGAAGCTGCTGAAGATGGCTGTGGGCATGCGGGCGCTGCTGGACACGGTGATGCAG
GCCCTGCCCCAGGTGGGGAACCTGGGACTTCTCTTCATGTTGTTGTTTTTCATCTTTGC
AGCTCTGGGCGTGGAGCTCTTTGGAGACCTGGAGTGTGACGAGACACACCCCTGTGAGG
GCCTGGGCCGTCATGCCACCTTTCGGAACTTTGGCATGGCCTTCCTAACCCTCTTCCGA
GTCTCCACAGGTGACAATTGGAATGGCATTATGAAGGACACCCTCCGGGACTGTGACCA
GGAGTCCACCTGCTACAACACGGTCATCTCGCCTATCTACTTTGTGTCCTTCGTGCTGA
CGGCCCAGTTCGTGCTAGTCAACGTGGTGATCGCCGTGCTGATGAAGCACCTGGAGGAG
AGCAACAAGGAGGCCAAGGAGGAGGCCGAGCTAGAGGCTGAGCTGGAGCTGGAGATGAA
GACCCTCAGCCCCCAGCCCCACTCGCCACTGGGCAGCCCCTTCCTCTGGCCTGGGGTCG
AGGGCCCCGACAGCCCCGACAGCCCCAAGCCTGGGGCTCTGCACCCAGCGGCCCACGCG
AGATCAGCCTCCCACTTTTCCCTGGAGCACCCCACGATGCAGCCCCACCCCACGGAGCT
GCCAGGACCAGACTTACTGACTGTGCGGAAGTCTGGGGTCAGCCGAACGCACTCTCTGC
CCAATGACAGCTACATGTGTCGGCATGGGAGCACTGCCGAGGGGCCCCTGGGACACAGG
GGCTGGGGGC
```

FIG. 1C

```
TCCCCAAAGCTCAGTCAGGCTCCGTCTTGTCCGTTCACTCCCAGCCAGCAGATACC
AGCTACATCCTGCAGCTTCCCAAAGATGCACCTCATCTGCTCCAGCCCCACAGCGC
CCCAACCTGGGGCACCATCCCCAAACTGCCCCCACCAGGACGCTCCCCTTTGGCTC
AGAGGCCACTCAGGCGCCAGGCAGCAATAAGGACTGACTCCTTGGACGTTCAGGGT
CTGGGCAGCCGGGAAGACCTGCTGGCAGAGGTGAGTGGGCCCTCCCCGCCCCTGGC
CCGGGCCTACTCTTTCTGGGGCCAGTCAAGTACCCAGGCACAGCAGCACTCCCGCA
GCCACAGCAAGATCTCCAAGCACATGACCCCGCCAGCCCCTTGCCCAGGCCCAGAA
CCCAACTGGGGCAAGGGCCCTCCAGAGACCAGAAGCAGCTTAGAGTTGGACACGGA
GCTGAGCTGGATTTCAGGAGACCTCCTGCCCCCTGGCGGCCAGGAGGAGCCCCCAT
CCCCACGGGACCTGAAGAAGTGCTACAGCGTGGAGGCCCAGAGCTGCCAGCGCCGG
CCTACGTCCTGGCTGGATGAGCAGAGGAGACACTCTATCGCCGTCAGCTGCCTGGA
CAGCGGCTCCCAACCCCACCTGGGCACAGACCCTCTAACCTTGGGGGCCAGCCTC
TTGGGGGGCCCGGGAGCCGGCCCAAGAAAAACTCAGCCCGCCTAGTATCACCATA
GACCCCCCGAGAGCCAAGGTCCTCGGACCCCGCCCAGCCCTGGTATCTGCCTCCG
GAGGAGGGCTCCGTCCAGCGACTCCAAGGATCCCTTGGCCTCTGGCCCCCCTGACA
GCATGGCTGCCTCGCCCTCCCCAAAGAAAGATGTGCTGAGTCTCTCCGGTTTATCC
TCTGACCCAGCAGACCTGGACCCCTGA
```

FIG. 2A

SEQ.ID.NO.4. The nucleotide sequence of human calcium channel alpha1G-c is shown including 522 bp 5' UT and 397 bp 3'UT.

```
CCGGGTCGACCCACGCGTCCGGATCCCTCCTCCCCTCCCCGCCGCCTGGCGCGGAG
CCGGGACGATGCTGACCCCTTAGATCCGGCTCCAGCTGCGCCGCGGGAAGAGGGGGC
GCCCCTCCCCGGACCCCCGCCCTCCGCCGCTGCCCCCCTTTTCGTTCGCCCTCTCGG
GGCGGCTTCGCCGAAGGTAGCGCCGAATCCGGCAACCGGAGCCTGGGCGCGAAGCGA
AGAAGCCGGAACAAAGTGAGGGGGAGCCGGCCGGCTGGCCCGGGAAGCCCCAGGGGC
GCAGGGGAAGCGGGACTCGCGCCGGGCGGGGTTTCCCTGCGCCCCGGCGCCCCGCGG
GCAGCATGCCCCTGCGGGCAGGGGGAGCTGGGCTGAACTGGCCCTCCCGGGGGCTCA
GCTTGCGCCCTAGAGCCCACCAGATGTGCCCCCGCCGGGGCCCCCGGGTTGCGTGAG
GACACCTCCTCTGAGGGGCGCCGCTTGCCCCTCTCCGGATCGCCCGGGGCCCCGGCT
GGCCAGAGGATGGACGAGGAGGAGGATGGAGCGGGCGCCGAGGAGTCGGGACAGCCC
CGGAGCTTCATGCGGCTCAACGACCTGTCGGGGGCCGGGGGCCGGCCGGGGCCGGGG
TCAGCAGAAAAGGACCCGGGCAGCGCGGACTCCGAGGCGGAGGGGCTGCCGTACCCG
GCGCTGGCCCCGGTGGTTTTCTTCTACTTGAGCCAGGACAGCCGCCCGCGGAGCTGG
TGTCTCCGCACGGTCTGTAACCCCTGGTTTGAGCGCATCAGCATGTTGGTCATCCTT
CTCAACTGCGTGACCCTGGGCATGTTCCGGCCATGCGAGGACATCGCCTGTGACTCC
CAGCGCTGCCGGATCCTGCAGGCCTTTGATGACTTCATCTTTGCCTTCTTTGCCGTG
GAGATGGTGGTGAAGATGGTGGCCTTGGGCATCTTTGGGAAAAAGTGTTACCTGGGA
GACACTTGGAACCGGCTTGACTTTTTCATCGTCATCGCAGGGATGCTGGAGTACTCG
CTGGACCTGCAGAACGTCAGCTTCTCAGCTGTCAGGACAGTCCGTGTGCTGCGACCG
CTCAGGGCCATTAACCGGGTGCCCAGCATGCGCATCCTTGTCACGTTGCTGCTGGAT
ACGCTGCCCATGCTGGGCAACGTCCTGCTGCTCTGCTTCTTCGTCTTCTTCATCTTC
GGCATCGTCGGCGTCCAGCTGTGGGCAGGGCTGCTTCGGAACCGATGCTTCCTACCT
GAGAATTTCAGCCTCCCCCTGAGCGTGGACCTGGAGCGCTATTACCAGACAGAGAAC
GAGGATGAGAGCCCCTTCATCTGCTCCCAGCCACGCGAGAACGGCATGCGGTCCTGC
AGAAGCGTGCCCACGCTGCGCGGGGACGGGGGCGGTGGCCCACCTTGCGGTCTGGAC
TATGAGGCCTACAACAGCTCCAGCAACACCACCTGTGTCAACTGGAACCAGTACTAC
ACCAACTGCTCAGCGGGGAGCACAACCCCTTCAAGGGCGCCATCAACTTTGACAAC
ATTGGCTATGCCTGGATCGCCATCTTCCAGGTCATCACGCTGGAGGGCTGGGTCGAC
ATCATGTACTTTGTGATGGATGCTCATTCCTTCTACAATTTCATCTACTTCATCCTC
CTCATCATCGTGGGCTCCTTCTTCATGATCAACCTGTGCCTGGTGGTGATTGCCACG
CAGTTCTCAGAGACCAAGCAGCGGGAAAGCCAGCTGATGCGGGAGCAGCGTGTGCGG
TTCCTGTCCAACGCCAGCACCCTGGCTAGCTTCTCTGAGCCCGGCAGCTGCTATGAG
GAGCTGCTCAAGTACCTGGTGTACATCCTTCGTAAGGCAGCCCGCAGGCTGGCTCAG
GTCTCTCGGGCAGCAGGTGTGCGGGTTGGGCTGCTCAGCAGCCCAGCACCCCTCGGG
GGCCAGGAGACCCAGCCCAGCAGCAGCTGCTCTCGCTCCCACCGCCGCCTATCCGTC
CACCACCTGGTGCACCACCACCACCACCATCACCACCACTACCACCTGGGCAATGGG
ACGCTCAGGGCCCCCGGGCCAGCCCGGAGATCCAGGACAGGGATGCCAATGGGTCC
CGCAGGCTCATGCTGCCACCACCCTCGACGCCTGCCCTCTCCGGGGCCCCCCTGGT
GGCGCAGAGTCTGTGCACAGCTTCTACCATGCCGACTGCCACTTAGAGCCAGTCCGC
TGCCAGGCGCCCCCTCCCAGGTCCCCATCTGAGGCATCCGGCAGGACTGTGGGCAGC
GGGAAGGTGTATCCCACCGTGCACACCAGCCCTCCACCGGAGACGCTGAAGGAGAAG
GCACTAGTAGAGGTGGCTGCCAGCTCTGGGCCCCAACCCTCACCAGCCTCAACATC
CCACCCGGGCCCTACAGCTCCATGCACAAGCTGCTGGAGACACAGAGTACAGGTGCC
TGCCAAAGCTCTTGCAAGATCTCCAGCCCTTGCTTGAAAGCAGACAGTGGAGCCTGT
GGTCCAGACAGCTGCCCCTACTGTGCCCGGGCCGGGGCAGGGGAGGTGGAGCTCGCC
GACCGTGAAATGCCTGACTCAGACAGCGAGGCAGTTTATGAGTTCACACAGGATGCC
CAGCACAGCGACCTCCGGGACCCCCACAGCCGGCGGCAACGGAGCCTGGGCCCAGAT
GCAGAGCCCAGC
```

FIG. 2B

```
TCTGTGCTGGCCTTCTGGAGGCTAATCTGTGACACCTTCCGAAAGATTGTGGACAGCAAG
TACTTTGGCCGGGGAATCATGATCGCCATCCTGGTCAACACACTCAGCATGGGCATCGAA
TACCACGAGCAGCCCGAGGAGCTTACCAACGCCCTAGAAATCAGCAACATCGTCTTCACC
AGCCTCTTTGCCCTGGAGATGCTGCTGAAGCTGCTTGTGTATGGTCCCTTTGGCTACATC
AAGAATCCCTACAACATCTTCGATGGTGTCATTGTGGTCATCAGCGTGTGGGAGATCGTG
GGCCAGCAGGGGGCGGCCTGTCGGTGCTGCGGACCTTCCGCCTGATGCGTGTGCTGAAG
CTGGTGCGCTTCCTGCCGGCGCTGCAGCGGCAGCTGGTGGTGCTCATGAAGACCATGGAC
AACGTGGCCACCTTCTGCATGCTGCTTATGCTCTTCATCTTCATCTTCAGCATCCTGGGC
ATGCATCTCTTCGGCTGCAAGTTTGCCTCTGAGCGGGATGGGGACACCCTGCCAGACCGG
AAGAATTTTGACTCCTTGCTCTGGGCCATCGTCACTGTCTTTCAGATCCTGACCCAGGAG
GACTGGAACAAAGTCCTCTACAATGGTATGGCCTCCACGTCGTCCTGGGCGGCCCTTTAT
TTCATTGCCCTCATGACCTTCGGCAACTACGTGCTCTTCAATTTGCTGGTCGCCATTCTG
GTGGAGGGCTTCCAGGCGGAGGAAATCAGCAAACGGGAAGATGCGAGTGGACAGTTAAGC
TGTATTCAGCTGCCTGTCGACTCCCAGGGGGGAGATGCCAACAAGTCCGAATCAGAGCCC
GATTTCTTCTCACCCAGCCTGGATGGTGATGGGACAGGAAGAAGTGCTTGGCCTTGGTG
TCCCTGGGAGAGCACCCGGAGCTGCGGAAGAGCCTGCTGCCGCCTCTCATCATCCACACG
GCCGCCACACCCATGTCGCTGCCCAAGAGCACCAGCACGGGCCTGGGCGAGGCGCTGGGC
CCTGCGTCGCGCCGCACCAGCAGCAGCGGGTCGGCAGAGCCTGGGGCGGCCCACGAGATG
AAGTCACCGCCCAGCGCCCGCAGCTCTCCGCACAGCCCTGGAGCGCTGCAAGCAGCTGG
ACCAGCAGGCGCTCCAGCCGGAACAGCCTCGGCCGTGCACCCAGCCTGAAGCGGAGAAGC
CCAAGTGGAGAGCGGCGGTCCCTGTTGTCGGGAGAAGGCCAGGAGAGCCAGGATGAAGAG
GAGAGCTCAGAAGAGGAGCGGGCCAGCCCTGCGGGCAGTGACCATCGCCACAGGGGGTCC
CTGGAGCGGGAGGCCAAGAGTTCCTTTGACCTGCCAGACACACTGCAGGTGCCAGGGCTG
CATCGCACTGCCAGTGGCCGAGGGTCTGCTTCTGAGCACCAGGACTGCAATGGCAAGTCG
GCTTCAGGGCGCCTGGCCCGGGCCCTGCGGCCTGATGACCCCCACTGGATGGGGATGAC
GCCGATGACGAGGGCAACCTGAGCAAAGGGGAACGGGTCCGCGCGTGGATCCGAGCCCGA
CTCCCTGCCTGCTGCCTCGAGCGAGACTCCTGGTCAGCCTACATCTTCCCTCCTCAGTCC
AGGTTCCGCCTCCTGTGTCACCGGATCATCACCCACAAGATGTTCGACCACGTGGTCCTT
GTCATCATCTTCCTTAACTGCATCACCATCGCCATGGAGCGCCCCAAAATTGACCCCCAC
AGCGCTGAACGCATCTTCCTGACCCTCTCCAATTACATCTTCACCGCAGTCTTTCTGGCT
GAAATGACAGTGAAGGTGGTGGCACTGGGCTGGTGCTTCGGGGAGCAGGCGTACCTGCGG
AGCAGTTGGAACGTGCTGGACGGGCTGTTGGTGCTCATCTCCGTCATCGACATTCTGGTG
TCCATGGTCTCTGACAGCGGCACCAAGATCCTGGGCATGCTGAGGGTGCTGCGGCTGCTG
CGGACCCTGCGCCCGCTCAGGGTGATCAGCCGGGCGCAGGGGCTGAAGCTGGTGGTGGAG
ACGCTGATGTCCTCACTGAAACCCATCGGCAACATTGTAGTCATCTGCTGTGCCTTCTTC
ATCATTTTCGGCATCTTGGGGGTGCAGCTCTTCAAAGGGAAGTTTTTCGTGTGCCAGGGC
GAGGATACCAGGAACATCACCAATAAATCGGACTGTGCCGAGGCCAGTTACCGGTGGGTC
CGGCACAAGTACAACTTTGACAACCTTGGCCAGGCCCTGATGTCCCTGTTCGTTTTGGCC
TCCAAGGATGGTTGGGTGGACATCATGTACGATGGGCTGGATGCTGTGGGCGTGGACCAG
CAGCCCATCATGAACCACAACCCCTGGATGCTGCTGTACTTCATCTCGTTCCTGCTCATT
GTGGCCTTCTTTGTCCTGAACATGTTTGTGGGTGTGGTGGTGGAGAACTTCCACAAGTGT
CGGCAGCACCAGGAGGAAGAGGAGGCCCGGCGGCGGGAGGAGAAGCGCCTACGAAGACTG
GAGAAAAAGAGAAGGAGTAAGGAGAAGCAGATGGCTGAAGCCCAGTGCAAACCTTACTAC
TCCGACTACTCCCGCTTCCGGCTCCTCGTCCACCACTTGTGCACCAGCCACTACCTGGAC
CTCTTCATCACAGGTGTCATCGGGCTGAACGTGGTCACCATGGCCATGGAGCACTACCAG
CAGCCCCAGATTCTGGATGAGGCTCTGAAGATCTGCAACTACATCTTCACTGTCATCTTT
GTCTTGGAGTCAGTTTTCAAACTTGTGGCCTTTGGTTTCCGTCGGTTCTTCCAGGACAGG
TGGAACCAGCTGGACCTGGCCATTGTGCTGCTGTCCATCATGGGCATCACGCTGGAGGAA
ATCGAGGTCAACGCCTCGCTGCCCATCAACCCCACCATCATCCGCATCATGAGGGTGCTG
CGCATTGCCCGAGTGCTGAAGCTGCTGAAGATGGCTGTGGGCATGCGGGCGCTGCTGGAC
ACGGTGATGCAGGCCCTGCCCCAGGTGGGGAACCTGGGACTTCTCTTCATGTTGTTGTTT
TTCATCTTTGCAGCTCTGGGCGTGGAGCTCTTTGGAGACCTGGAGTGTGACGAGACACAC
CCCTGTGAGGGCCTGGGCCGT
```

FIG. 2C

```
CATGCCACCTTTCGGAACTTTGGCATGGCCTTCCTAACCCTCTTCCGAGTCTCCACA
GGTGACAATTGGAATGGCATTATGAAGGACACCCTCCGGGACTGTGACCAGGAGTCC
ACCTGCTACAACACGGTCATCTCGCCTATCTACTTTGTGTCCTTCGTGCTGACGGCC
CAGTTCGTGCTAGTCAACGTGGTGATCGCCGTGCTGATGAAGCACCTGGAGGAGAGC
AACAAGGAGGCCAAGGAGGAGGCCGAGCTAGAGGCTGAGCTGGAGCTGGAGATGAAG
ACCCTCAGCCCCAGCCCCACTCGCCACTGGGCAGCCCCTTCCTCTGGCCTGGGGTC
GAGGGCCCCGACAGCCCCGACAGCCCCAAGCCTGGGGCTCTGCACCCAGCGGCCCAC
GCGAGATCAGCCTCCCACTTTTCCCTGGAGCACCCCACGATGCAGCCCCACCCCACG
GAGCTGCCAGGACCAGACTTACTGACTGTGCGGAAGTCTGGGGTCAGCCGAACGCAC
TCTCTGCCCAATGACAGCTACATGTGTCGGCATGGGAGCACTGCCGAGGGGCCCCTG
GGACACAGGGCTGGGGGCTCCCCAAAGCTCAGTCAGGCTCCGTCTTGTCCGTTCAC
TCCCAGCCAGCAGATACCAGCTACATCCTGCAGCTTCCCAAAGATGCACCTCATCTG
CTCCAGCCCCACAGCGCCCCAACCTGGGGCACCATCCCCAAACTGCCCCCACCAGGA
CGCTCCCCTTTGGCTCAGAGGCCACTCAGGCGCCAGGCAGCAATAAGGACTGACTCC
TTGGACGTTCAGGGTCTGGGCAGCCGGGAAGACCTGCTGGCAGAGGTGAGTGGGCCC
TCCCCGCCCTGGCCCGGGCCTACTCTTTCTGGGGCCAGTCAAGTACCCAGGCACAG
CAGCACTCCCGCAGCCACAGCAAGATCTCCAAGCACATGACCCCGCCAGCCCCTTGC
CCAGGCCCAGAACCCAACTGGGGCAAGGGCCCTCCAGAGACCAGAAGCAGCTTAGAG
TTGGACACGGAGCTGAGCTGGATTTCAGGAGACCTCCTGCCCCCTGGCGGCCAGGAG
GAGCCCCCATCCCCACGGGACCTGAAGAAGTGCTACAGCGTGGAGGCCCAGAGCTGC
CAGCGCCGGCCTACGTCCTGGCTGGATGAGCAGAGGAGACACTCTATCGCCGTCAGC
TGCCTGGACAGCGGCTCCCAACCCCACCTGGGCACAGACCCCTCTAACCTTGGGGGC
CAGCCTCTTGGGGGGCCCGGGAGCCGGCCCAAGAAAAAACTCAGCCCGCCTAGTATC
ACCATAGACCCCCCGAGAGCCAAGGTCCTCGGACCCCGCCCAGCCCTGGTATCTGC
CTCCGGAGGAGGGCTCCGTCCAGCGACTCCAAGGATCCCTTGGCCTCTGGCCCCCCT
GACAGCATGGCTGCCTCGCCCTCCCCAAAGAAAGATGTGCTGAGTCTCTCCGGTTTA
TCCTCTGACCCAGCAGACCTGGACCCTGAGTCCTGCCCCACTTTCCCACTCACCTT
TCTCCACTGGGTGCCAAGTCCTAGCTCCTCCTCCTGGGCTATATTCCTGACAAAAGT
TCCATATAGACACCAAGGAGGCGGAGGCGCTCCTCCCTGCCTCAGTGGCTCTGGGTA
CCTGCAAGCAGAACTTCCAAAGAGAGTTAAAAGCAGCAGCCCCGGCAACTCTGGCTC
CAGGCAGAAGGAGAGGCCCGGTGCAGCTGAGGTTCCCGACACCAGAAGCTGTTGGGA
GAAAGCAATACGTTTGTGCAGAATCTCTATGTATATTCTATTTTATTAAATTAATTG
AATCTAGTATATGCGGGATGTACGACATTTTGTGACTGAAGAGACTTGTTTCCTTCT
ACTTTTATGTGTCTCAGAATATTTTTGA
```

FIG. 3

SEQ.ID.NO.5. Coding sequence for human calcium channel alpha1G-c (2273 amino acids)

```
MDEEEDGAGAEESGQPRSFMRLNDLSGAGGRPGPGSAEKDPGSADSEAEGLPYPALAP
VVFFYLSQDSRPRSWCLRTVCNPWFERISMLVILLNCVTLGMFRPCEDIACDSQRCRI
LQAFDDFIFAFFAVEMVVKMVALGIFGKKCYLGDTWNRLDFFIVIAGMLEYSLDLQNV
SFSAVRTVRVLRPLRAINRVPSMRILVTLLLDTLPMLGNVLLLCFFVFFIFGIVGVQL
WAGLLRNRCFLPENFSLPLSVDLERYYQTENEDESPFICSQPRENGMRSCRSVPTLRG
DGGGGPPCGLDYEAYNSSSNTTCVNWNQYYTNCSAGEHNPFKGAINFDNIGYAWIAIF
QVITLEGWVDIMYFVMDAHSFYNFIYFILLIIVGSFFMINLCLVVIATQFSETKQRES
QLMREQRVRFLSNASTLASFSEPGSCYEELLKYLVYILRKAARRLAQVSRAAGVRVGL
LSSPAPLGGQETQPSSSCSRSHRRLSVHHLVHHHHHHHHYHLGNGTLRAPRASPEIQ
DRDANGSRRLMLPPPSTPALSGAPPGGAESVHSFYHADCHLEPVRCQAPPPRSPSEAS
GRTVGSGKVYPTVHTSPPPETLKEKALVEVAASSGPPTLTSLNIPPGPYSSMHKLLET
QSTGACQSSCKISSPCLKADSGACGPDSCPYCARAGAGEVELADREMPDSDSEAVYEF
TQDAQHSDLRDPHSRRQRSLGPDAEPSSVLAFWRLICDTFRKIVDSKYFGRGIMIAIL
VNTLSMGIEYHEQPEELTNALEISNIVFTSLFALEMLLKLLVYGPFGYIKNPYNIFDG
VIVVISVWEIVGQQGGGLSVLRTFRLMRVLKLVRFLPALQRQLVVLMKTMDNVATFCM
LLMLFIFIFSILGMHLFGCKFASERDGDTLPDRKNFDSLLWAIVTVFQILTQEDWNKV
LYNGMASTSSWAALYFIALMTFGNYVLFNLLVAILVEGFQAEEISKREDASGQLSCIQ
LPVDSQGGDANKSESEPDFFSPSLDGDGDRKKCLALVSLGEHPELRKSLLPPLIIHTA
ATPMSLPKSTSTGLGEALGPASRRTSSSGSAEPGAAHEMKSPPSARSSPHSPWSAASS
WTSRRSSRNSLGRAPSLKRRSPSGERRSLLSGEGQQSQDQEESSEEERASPAGSDHRH
RGSLEREAKSSFDLPDTLQVPGLHRTASGRGSASEHQDCNGKSASGRLARALRPDDPP
LDGDDADDEGNLSKGERVRAWIRARLPACCLERDSWSAYIFPPQSRFRLLCHRIITHK
MFDHVVLVIIFLNCITIAMERPKIDPHSAERIFLTLSNYIFTAVFLAEMTVKVVALGW
CFGEQAYLRSSWNVLDGLLVLISVIDILVSMVSDSGTKILGMLRVLRLLRTLRPLRVI
SRAQGLKLVVETLMSSLKPIGNIVVICCAFFIIFGILGVQLFKGKFFVCQGEDTRNIT
NKSDCAEASYRWVRHKYNFDNLGQALMSLFVLASKDGWVDIMYDGLDAVGVDQQPIMN
HNPWMLLYFISFLLIVAFFVLNMFVGVVVENFHKCRQHQEEEEARRREEKRLRRLEKK
RRSKEKQMAEAQCKPYYSDYSRFRLLVHHLCTSHYLDLFITGVIGLNVVTMAMEHYQQ
PQILDEALKICNYIFTVIFVLESVFKLVAFGFRRFFQDRWNQLDLAIVLLSIMGIPLE
QIEVNASLPINPTIIRIMRVLRIARVLKLLKMAVGMRALLDTVMQALPQVGNLGLLFM
LLFFIFAALGVELFGDLECDETHPCEGLGRHATFRNFGMAFLTLFRVSTGDNWNGIMK
DTLRDCDQESTCYNTVISPIYFVSFVLTAQFVLVNVVIAVLMKHLEESNKEAKEEAEL
EAELELEMKTLSPQPHSPLGSPFLWPGVEGPDSPDSPKPGALHPAAHARSASHFSLEH
PTMQPHPTELPGPDLLTVRKSGVSRTHSLPNDSYMCRHGSTAEGPLGHRGWGLPKAQS
GSVLSVHSQPADTSYILQLPKDAPHLLQPHSAPTWGTIPKLPPPGRSPLAQRPLRRQA
AIRTDSLDVQGLGSREDLLAEVSGPSPPLARAYSFWGQSSTQAQQHSRSHSKISKHMT
PPAPCPGPEPNWGKGPPETRSSLELDTELSWISGDLLPPGGQEEPPSPRDLKKCYSVE
AQSCQRRPTSWLDEQRRHSIAVSCLDSGSQPHLGTDPSNLGGQPLGGPGSRPKKKLSP
PSITIDPPESQGPRTPPSPGICLRRRAPSSDSKDPLASGPPDSMAASPSPKKDVLSLS
GLSSDPADLDP
```

DNA ENCODING HUMAN ALPHA1G-C T-TYPE CALCIUM CHANNEL

BACKGROUND OF THE INVENTION

Voltage activated calcium channels play important roles including neuroexcitation, neurotransmitter and hormone secretion, and regulation of gene transcription through Ca-dependent transcription factors. Their functions depend in part on their cellular localization and their gating properties (characteristics of their opening, inactivation, deactivation, and recovery from inactivation). Five general classes of voltage activated calcium channels have been observed in various neuronal and non-neuronal tissues. The complement of channel subunits and the subcellular localization of the expressed voltage activated calcium channels determine the functional cellular properties.

Diversity of Voltage-gated Ca Channels Fall into Two Major Categories: Low Voltage Activated (LVA) and High Voltage Activated (HVA)

A conserved general structure for all cloned voltage-gated calcium channel alpha subunits (the pore-forming subunit) has been identified. It consists of 4 domains with homology to the domains present in voltage-gated K and Na channels. Each domain contains 6 membrane spanning regions (S1–S6) and a pore region (P) located between S5 and S6. The extracellular loops are generally very short; intracellular loops contain sites that are modulated by phosphorylation and can interact with other effectors. However, there are notable differences in the lengths of the S5–S6 loop of domain I and the intracellular loop between domains I and II among alpha subunits.

Different calcium channels are best distinguished by their pharmacological profiles since their electrophysiological properties differ depending on the cell type or tissue in which they are expressed, presumably because of modulation by cellular proteins, for instance kinases, and also auxiliary calcium channel subunits.

The HVA channel classes are thought to be composed of at least 3 or 4 different subunits: α1 (which contains the pore), beta (β) and α2δ. In skeletal muscle a γ subunit also co-precipitates with the skeletal channel complex. Recently two gamma-like subunits have been cloned from brain—one of which is the gene mutated in the stargazer mutant mouse (Black et al., 1999; Letts et al., 1998). The subunit composition has been proved for only the skeletal L-type (α1 α2δ β γ) and brain N-type (α1 α2δ β) channels (Perez-Reyes and Schneider, 1995). These channels generally require large membrane depolarizations for activation (~30 mV from the resting potential (RP)). Four classes of HVA calcium channels have been identified on the basis of electrophysiological, pharmacological and molecular data. These classes include L-type (encoded by at least 4 genes (including a α1 subunits α1S (skeletal muscle), α1C, α1D (neuroendocrine), and α1F (retinal)), N-type (α1B; (Williams et al., 1992)), P/Q-type (α1A) and R-type (encoded by at least the α1E gene).

HVA α1 families are strongly affected by co-expression of the cytoplasmically localized β subunit, particularly the expression levels of functional cell surface channels and the electrophysiological response of the channel (ie., kinetics). β subunits interact with a specific sequence in the I-II intracellular loop to increase the number of functional channels and alter the activation and inactivation properties of the channel complex (Furukawa et al., 1998). There are at least 4β genes that are alternatively spliced (β1a-c; β2a-c; β3; β4;(Perez-Reyes and Schneider, 1995)); the effect of each of these βs on α1 function appears to depend on the α1 class. Interestingly, mutants in β (Cchβ4) produce ataxia and seizures in the lethargic (lh) mouse (Burgess et al., 1997). α2δ subunits also modulate α1 function and the known gene co-segregates with malignant hyperthermia phenotype in certain families (Iles et al., 1994).

The physiological roles of HVA channels depend on subcellular location of the channel and tissue type. Subcellular location varies among tissues but have been shown to be important in neurotransmitter and hormone release, action potential duration, excitation-contraction coupling in muscle cells, and gene expression (Miller, 1987).

There are at least three genes in the T-type family of LVA calcium channels (α1G, α1H, and α1I) (Perez-Reyes, 1998). Their structure differs from that of the HVA channels in a number of important ways. The I-II intracellular linker is much longer (~400 amino acids) than that of the known HVA channels. The Domain I S5-P extracellular linker is longer than that of the HVA channels and may be a good target for drug interactions with this channel. β does not appear to be associated with α1 in this class and they lack the canonical sequence that is known to be crucial for beta subunit binding (Lambert et al., 1997; Leuranguer et al., 1998). Anti-sense experiments directed against all known beta's show a decrease in the expression of HVA calcium channels but not LVA calcium channels in nodose ganglion neurons (Lambert et al., 1997).

Other proteins or cellular environments may be required for robust T-channel expression since α1G expressed in oocytes or HEK293 cells produces dramatically different current magnitudes in these two cell types (Perez-Reyes, 1998).

T-type calcium currents have been observed in vivo in many cell types in the peripheral and central nervous systems including thalamus, inferior olive, cerebellar Purkinje cells, lateral habenular cells, dorsal horn neurons, sensory neurons (DRG, nodose), cholinergic forebrain neurons, hippocampal interneurons, CA1, CA3 dentate gyrus pyramidal cells, basal forebrain neurons, amygdaloid neurons (Talley et al., 1999). T-type channels are prominent in the soma and dendrites of neurons that reveal robust Ca-dependent burst firing behaviors such as the thalamic relay neurons and cerebellar Purkinje cells (Huguenard, 1996).

Physiological Roles and Therapeutic Areas

T-type calcium channels are involved in the generation of low threshold spikes to produce burst firing (Huguenard, 1996). These channels differ from HVA channels in that they have some probability of opening at the resting membrane potential. Because their steady state inactivation curve is shifted toward negative voltages compared to HVA channels (ie., half the channels are not inactivated and are able to be opened by a depolarizing voltage step at voltages more negative than the resting membrane potential (RP)), there is a window current near the RP (ie., a portion of the T-channels are open at RP). Low threshold spikes and rebound burst firing is prominent in neurons from inferior olive, thalamus, hippocampus and neocortex (Huguenard, 1996).

T-type channels promote oscillatory behavior which has important consequences for epilepsy. The ability of a cell to fire low threshold spikes is critical in the genesis of oscillatory behavior and increased burst firing (groups of action potentials separated by about 50–100 ms). T-type calcium channels are thought to play a significant role in absence epilepsy, a type of generalized non-convulsive seizure. The evidence that voltage-gated calcium currents contribute to the epileptogenic discharge, including seizure maintenance and propagation includes 1) a specific enhancement of T-type currents in the reticular thalamic (nRT) neurons which are hypothesized to be involved in the genesis of epileptic seizures in a rat genetic model (GAERS) for absence epilepsy (Tsakiridou et al., 1995); 2) antiepileptics against absence petit mal epilepsy (ethosuximide and dimethadione) have been shown at physiologically relevant doses to partially depress T-type currents in thalamic (ventrobasal complex) neurons (Coulter et al., 1989; Kostyuk et al., 1992); and 3) T-type calcium channels underlie the intrinsic bursting properties of particular neurons that are hypothesized to be involved in epilepsy (nRT, thalamic relay and hippocampal pyramidal cells) (Huguenard, 1996). The rat α1G is highly expressed in thalamocortical relay cells (TCs) which are capable of generating prominent $Ca^{2+}$-dependent low-threshold spikes (Talley et al., 1999).

T-type channels play a critical role in thalamic oscillations and cortical synchrony, and their involvement has been directly implicated in the generation of cortical spike waves that are thought to underlie absence epilepsy and the onset of sleep (McCormick and Bal, 1997). Oscillations of neural networks are critical in normal brain function such during sleep-wave cycles. It is widely recognized that the thalamus is intimately involved in cortical rhythmogenesis. Thalamic neurons most frequently exhibit tonic firing (regularly spaced spontaneous firing) in awake animals, whereas phasic burst firing is typical of slow-wave sleep and may account for the accompanying spindling in the cortical EEG. The shift to burst firing occurs as a result of activation of a low threshold $Ca^{2+}$ spike which is stimulated by synaptically mediated inhibition (ie., activated upon hyperpolarization of the RP). The reciprocal connections between pyramidal neurons in deeper layers of the neocortex, cortical relay neurons in the thalamus, and their respective inhibitory interneurons are believed to form the elementary pacemaking circuit.

T-type channels contribute to synaptic potentiation at the postsynaptic level since small changes in membrane potential (Vm) (either depolarizations (epsps; excitatory postsynaptic potentials) or hyperpolarizations (ipsps (inhibitory postsynaptic potentials); anode break exhaltation or rebound burst firing) can open T-type calcium channels. At the hyperpolarized Vm during the ipsp more T-type channels become available to open (they have recovered from inactivation) so that upon repolarization to the RP, a larger proportion of T channels are opened and this produces anode break exhaltation, a robust rebound burst firing as the low threshold Ca spike reaches threshold for Na channel activation and action potential generation. A burst of action potentials ride on top of the Ca-dependent depolarization. This phenomenon is particularly prominent in reticular thalamic neurons (Huguenard, 1996).

T-type channels can be involved in transmitter release. In cells where T-channels are located at the presynaptic terminal, they promote neurotransmitter release (Ahnert-Hilger et al., 1996; Arnoult et al., 1997)

T-type channels contribute to spontaneous fluctuations in intracellular Ca concentrations $[Ca]_i$. They are important in pacemaker activity and therefore heart rate in the heart, and in vesicle release from non-excitable cells (Ertel et al., 1997).

T-type calcium currents are expressed differentially in different subpopulations of adult rat dorsal root ganglion (DRG) neurons. T-type currents were present at moderate densities in small diameter Type 1 and 3 cells, the former having TTX-resistant Na currents, long duration action potentials and capsaicin sensitivity (consistent with a C type nociceptive neuron) and the latter having short action potential durations, no capsaicin sensitivity (consistent with a Aδ nociceptive or Aα/β neurons) (Cardenas et al., 1995). There appear to be different types of LVA currents expressed in adult rat sensory neurons based on differential sensitivity to nM concentrations of nimodipine (Formenti et al., 1993). Because of the role of the T type calcium channel in contributing to near threshold membrane excitability, selective suppression of the T channels will decrease neuronal hyperexcitability (painful neuropathies) and raise the threshold for the perception of pain (central pain syndromes).

A specific blocker for T-type calcium channels in the pacemaker cells and conduction fibers in the heart might demonstrate "pure" bradycardic (slowing the heart rate) properties since T channels are not usually present in the ventricular myocytes of man. Drugs that block the T-type channel in specific conformational states might allow treatment of tachycardia (by decreasing the heart rate) while having little effect on the inotropic properties of the normal heart (Rousseau et al., 1996). A cardiomyopathic disease (genetic Syrian hamster model) is a result of Ca-overload due to an increased expression of T-type calcium channels in ventricular myocytes (Sen and Smith, 1994). There are increased T-type currents in atrial myocytes from adult rats with growth hormone-secreting tumors (Xu and Best, 1990). A specific T-type calcium channel blocker would act as a cardioprotectant in these cases.

T-type channels in adrenal zona fasciculata cells of the adrenal cortex have been shown to modulate cortisol secretion (Enyeart et al., 1993). Cortisol is the precursor for glucocorticoids and prolonged exposure to glucocorticoids causes breakdown of peripheral tissue protein, increased glucose production by the liver and mobilization of lipid from the fat depots. Furthermore, individuals suffering from anxiety and stress produce too high levels of glucocorticoids and drugs that would regulate these levels are sought after (eg., antagonists to CRF).

T-type calcium channels may be involved in release of nutrients from testis Sertoli cells. T-type calcium channels are expressed on immature rat Sertoli cells (Lalevee et al., 1997). Sertoli cells are testicular cells that are thought to play a major role in sperm production. The intimate juxtaposition of the developing germ cells with the Sertoli cells suggests the latter pay a role in supporting and nurturing the gametes. Sertoli cells secrete a number of proteins including transport proteins, hormones and growth factors, enzymes which regulate germinal cell development and other biological processes related to reproduction (Griswold, 1988). They secrete the peptide hormone inhibin B, an important negative feedback signal to the anterior pituitary. They assist in spermiation (the final detachment of the mature spermatozoa from the Sertoli cell into the lumen) by releasing plasminogen activator which produces proteolytic enzymes. While the role of T channels in not known, they may be important in the release of nutrients, inhibin B, and/or plasminogen activator.

Inhibition of T-type calcium channels in sperm during gamete interaction inhibits zona pellucida-dependent $Ca^{2+}$ elevations and inhibits acrosome reactions, thus directly linking sperm T-type calcium channels to fertilization (Arnoult et al., 1996).

T-type calcium channels have also been implicated in cellular growth and proliferation, particularly in the cardiovascular system (Katz, 1999; Lijnen and Petrov, 1999; Richard and Nargeot, 1998; Wang et al., 1993).

Tremor can be controlled through the basal ganglia and the thalamus, regions in which T type calcium channels are strongly expressed (Talley et al., 1999). T-type calcium channels have been implicated in the pathophysiology of tremor since the anti-epileptic drug ethosuximide is used for treating tremor, in particular, tremor associated with Parkinson's disease, essential tremor, or cerebellar disease (U.S. Pat. No. 4,981,867; D. A. Prince).

Pharmacology

There are no known specific blockers of the T-type class of calcium channel. There are ions (ex. $Ni^{+2}$) that are more effective toward blocking T-type calcium channels vs. HVA channels, and there are a few drugs that block T channels with higher affinity than HVA channels. A number of pharmacological blockers have differential effects on T type calcium currents expressed in different cell types (see Table 1 from (Todorovic and Lingle, 1998)), however there is a diversity of pharmacological profiles of T-type currents. The differential sensitivity of the currents to antagonists may be due to different subunit structure (Perez-Reyes, 1998) as well as cellular environments. T-type calcium channel alpha subunit genes, like the genes for HVA channels, reveal alternative splicing (Lee et al., 1999 Biophys J 76:A408). Extracellular and intracellular loops of individual T-type calcium channel clones show marked diversity amongst themselves and even less homology to HVA channels.

Mibefradil ((1S,2S)-2-[2-[[3-(1H-benzimidazol-2-yl) propyl]methyl-amino]ethyl]-6-fluoro-1-isopropyl-1,2,3,4-tetrahydronaphthalen-2-yl methoxyacetate) blocks the T-type calcium channel by preferentially intereacting with inactivated state. Thus, in a cell type with a relatively low RP (~-50 mV) such as the smooth muscle cells, nearly all T channels will be blocked by mibefradil, whereas in cells with a very negative RP such as cardiac myocytes most of the T channels are not inactivated and therefore will not be blocked by mibefradil (Bezprozvanny and Tsien, 1995). Mibefradil had a complex blocking action on the mouse alpha1G when applied from holding potentials of –60 and could best be fit by fitting to 2 populations of sites (Klugbauer et al., 1999). The high affinity component was reduced at –100 mV. The most prominent (low affinity) site had an $IC_{50}$ value for mibefradil of ~400 nM.

Ethosuximide is used to treat absence epilepsy and at therapeutically relevant concentrations (0.25–0.75 mM) (Sherwin, 1989) partially blocks T-type currents in some preparations (Coulter et al., 1989). Ethosuximide has different affinities for T-type calcium channels in different tissues. The majority of T type currents from guinea pig or rat ventrobasal thalamic neurons revealed an $IC_{50}$ for mibefradil of ~500 μM and a maximal block of ~40% block at 1 mM (Coulter et al., 1989). Interestingly, there was no effect of ethosuximide on T-currents in 25% of the TCs tested (Coulter et al., 1989). In hippocampal CA3 neurons, all components of the LVCC were insensitive to ethosuximide at 250 μM or 1 mM. If T-type calcium channels underlie the LVCC in these cells, then the drug had no effect on these T-type calcium channels (Avery and Johnston, 1996). The T-type calcium channels from dorsal root ganglion neurons from one-day-old rats have higher affinity for ethosuximide than thalamic neurons (Kd for T-current is 7 μM vs 15 μM for L-type current) with a maximal block of 100% (Kostyuk et al., 1992). The human alpha1H is insensitive to ethosuximide (Williams et al., WO 9928342; Williams et al., 1999).

Ni2+ is thought to act not only on the pore region but also at another unknown location on the channel protein (Zamponi et al., 1996). The mouse alpha1G has a very low sensitivity to $Ni^{2+}$ as opposed to other T-type channels (Klugbauer et al., 1999). The human alpha1H expressed in oocytes has an IC50 for $Ni^{2+}$ of about 6 μM (Williams et al., WO 9928342).

Amiloride, an antagonist at numerous receptors, channels and exchangers, is a low affinity antagonist at T-type calcium channels. There are noted differences in sensitivity of T currents to amiloride (Todorovic and Lingle, 1998). The effects of amiloide are highly variable depending on the cell type, with EC50's ranging from 50 to >1000 μM, suggesting that different levels of T-type channel expression in different cells or different channel complexes within different cells (Huguenard, 1996). For instance, the human alpha1H expressed in oocytes has an IC50 for amiloride of about 20 μM (Williams et al., WO 9928342).

NPPB (5-Nitro-2-(3-phenylpropylamino)benzoic acid) has been used to isolate N-type calcium channels (Stea et al., 1999) and was used in studies on the present invention to isolate T-type calcium channels. However, we found NPPB blocked halpha1G-c currents. NPPB has been shown to block voltage-sensitive calcium currents (Kirkup et al., 1996), and, more specifically, L-type calcium currents (Doughty et al., 1998). Interestingly, NPPB reduced the $Ca^{2+}$ resting current and altered the spike frequency of isolated cockroach dorsal unpaired median neurons (Heine and Wicher, 1998). The resting calcium current may be mediated by a T-type calcium channel, but this has yet to be confirmed.

SUMMARY OF THE INVENTION

A DNA molecule encoding a novel isoform of the human T-type low voltage activated calcium channel (alpha1G-c) has been cloned and characterized. The biological and structural properties of this protein is disclosed, as is the amino acid and nucleotide sequence. The recombinant protein is useful to identify modulators of the alpha1G-c calcium channel. Modulators identified in the assays disclosed herein are useful as therapeutic agents and are candidates for the treatment disorders that are mediated by human alpha1G-c activity. Such activities that may be mediated by human alpha1G-c include, epilepsy, schizophrenia, depression, sleep disorders, stress, endocrine disorders, respiratory disorder, peripheral muscle disorders, muscle excitability, Cushing's disease, fertilization, contraception, disorders involving neuronal firing regulation, respiratory disorders, hypertension, cardiac rhythm, potentiation of synaptic signals, improving arterial compliance in systolic hypertension, vascular tone such as by decreasing vascular swelling, cellular growth (protein synthesis, cell differentiation, and proliferation), cardiac hypertrophy, cardiac fibrosis, atherosclerosis, cardiovascular disorders, including but not limited to: myocardial infarct, cardiac arrhythmia, heart failure and angina pectoris. The recombinant DNA molecules, and portions thereof, are useful for isolating homologues of the DNA molecules, identifying and isolating genomic equivalents of the DNA molecules, and identifying, detecting or isolating mutant forms of the DNA molecules.

BRIEF DESCRIPTION OF THE DRAWINGS

FIG. 1, Panel A, Panel B and Panel C—The nucleotide sequence of coding region of human calcium channel alpha1G-c is shown (6822 bp including the stop codon).

FIG. 2, Panel A, Panel B and Panel C—The nucleotide sequence of human calcium channel alpha1G-c is shown including 511 bp 5' UT and 397 bp 3'UT.

FIG. 3—The amino acid sequence of human calcium channel alpha1G-c is shown (2273 amino acids).

DETAILED DESCRIPTION

Figure 4:
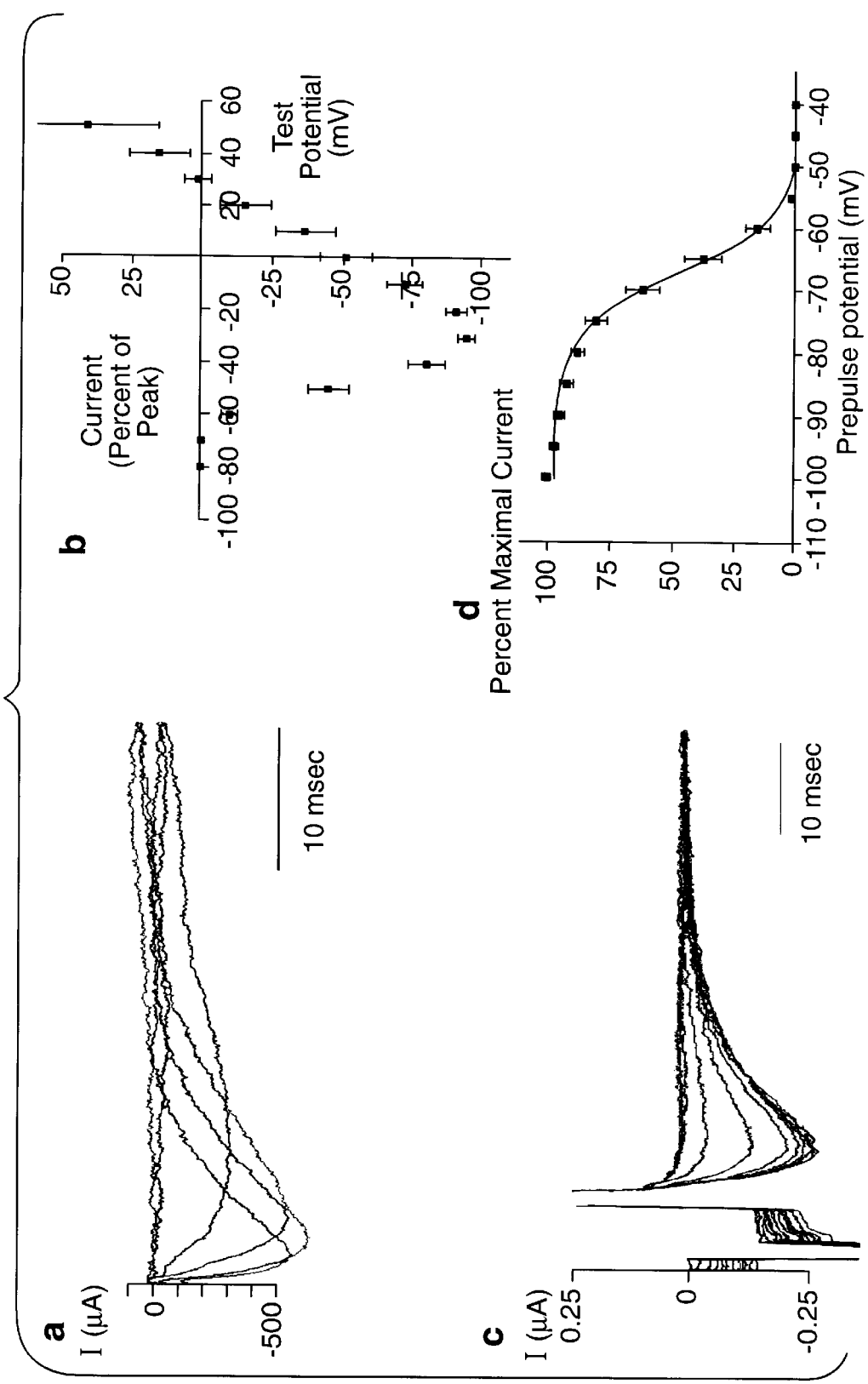
FIG. 4—Functional expression of human calcium channel alpha1G-c in Xenopus oocytes is shown: activation by depolarizing voltage steps (a,b) and steady state inactivation (c,d). a) An oocyte bathed in 40 mM BaCl$_2$ saline was challenged with a depolarizing voltage protocol from a holding potential of −100 mV. 40 msec test pulses were applied from −70 to −20 mV in increments of 10 mV. b) The current-voltage relationship obtained from 9 oocytes bathed in ND96. Currents activated near −60 mV and reversed sign near +30 mV. Peak currents were elicited by steps to about −30 mV. c) The voltage-dependence of inactivation of an oocyte bathed in 40 mM BaCl$_2$ was determined using a standard voltage protocol. Four sec voltage steps to −100 to −45 mV (in increments of 5 mV) were followed by a 5 msec step to −100 mV, followed by a step to −30 mV. The currents elicited at −30 mV are shown after the positive-going capacitative transient. The prepulse voltage that inactivated half the channels ($V_{0.5}$) was about −70 mV. d) The voltage dependence of inactivation is shown for oocytes bathed in ND96 (n=9 experiments).

The present invention relates to DNA encoding human calcium channel alpha1G-c that was isolated from a human thalamus cDNA library. Human calcium channel alpha1G-c, as used herein, refers to protein that can specifically function as a low voltage activated calcium channel.

The sequence presented in this invention is a homolog of the rat alpha1G accession # AF027984 (Perez-Reyes et al., 1998), and is similar to the human alpha1G "a" isoform (accession # AF126966) with the exception that the sequence presented herein contains a 23 amino acid insert in the second intracellular loop between domains I and II that is missing in both sequences. The 23 amino acid insert contains a putative CKII phosphorylation site at S971. This 23 amino acid insert is 91 and 87% identical to homologous sequences in rat (AF125161) and mouse (AJ012569), respectively, two proteins otherwise dissimilar to human alphaG-c since they contain an insert at alpha1G amino acid 1575. The putative casein kinase II phosphorylation site in the human alphaG-c insert is not conserved in the equivalent rat or mouse sequences. The previously described human full length cDNA (AF126966) produces functional channels (Monteil, a et al., 1999 Cloning and molecular characterization of a1G and a1I isoforms of human T-type Ca2+ channels. Biophys. Abst: A408) but a complete description of its functional and structural characteristics has not been reported. The present invention is thus the first report, to our knowledge, of a detailed characterization of the human alpha1G-c T-type calcium channel. There are 2 partial human sequences that are identical to regions of the present invention submitted by E. Perez-Reyes (AF029229; AF029228). AF029228 begins at alpha1G-c at amino acid 1186 and ends at amino acid 1504; AF029229 begins at amino acid 1827 and ends at the TGA stop codon.

The complete amino acid sequence of human calcium channel alpha1G has been previously described, however, the present invention is a novel isoform that was not previously known. This is the first reported cloning of a full length DNA molecule encoding the "c" isoform of the human calcium channel alpha1G. It is predicted that a wide variety of cells and cell types will contain the described channel.

Other cells and cell lines may also be suitable for use to isolate human calcium channel alpha1G-c. Selection of suitable cells may be done by screening for human calcium channel alpha1G-c activity in whole cells or cell extracts. Human calcium channel alpha1G-c activity can be monitored by direct measurement of a low depolarizing voltage-induced $Ca^{2+}$ influx or Ca currents through the human calcium channel alpha1G-c. Cells that possess human calcium channel alpha1G-c activity in this assay may be suitable for the isolation of human calcium channel alpha1G-c DNA or mRNA.

Any of a variety of procedures known in the art may be used to molecularly clone human calcium channel alpha1G-c. These methods include, but are not limited to, direct functional expression of the human calcium channel alpha1G-c genes following the construction of a human calcium channel alpha1G-c -containing cDNA library in an appropriate expression vector system. Another method is to screen human calcium channel alpha1G-c -containing cDNA library constructed in a bacteriophage or plasmid shuttle vector with a labelled oligonucleotide probe designed from the amino acid sequence of the human calcium channel alpha1G-c insert. An additional method consists of screening a human calcium channel alpha1G-c-containing cDNA library constructed in a bacteriophage or plasmid shuttle vector with a partial cDNA encoding the human calcium channel alpha1G-c protein. This partial cDNA is obtained by the specific PCR amplification of human calcium channel alpha1G-c DNA fragments through the design of degenerate oligonucleotide primers from the amino acid sequence of the purified human calcium channel alpha1G-c protein.

Another method is to isolate RNA from human calcium channel alpha1G-c-producing cells and translate the RNA into protein via an in vitro or an in vivo translation system. The translation of the RNA into a peptide a protein will result in the production of at least a portion of the human calcium channel alpha1G-c protein which an be identified by, for example, immunological reactivity with an anti-human calcium channel alpha1G-c antibody or by biological activity of human calcium channel alpha1G-c protein. In this method, pools of RNA isolated from human calcium channel alpha1G-c-producing cells can be analyzed for the presence of an RNA that encodes at least a portion of the human calcium channel alpha1G-c protein. Further fractionation of the RNA pool can be done to purify the human calcium channel alpha1G-c RNA from non-human calcium channel alpha1G-c RNA. The peptide or protein produced by this method may be analyzed to provide amino acid sequences, which in turn are used to provide primers for production of human calcium channel alpha1G-c cDNA, or the RNA used for translation can be analyzed to provide nucleotide sequences encoding human calcium channel alpha1G-c and produce probes for this production of human calcium channel alpha1G-c cDNA. This method is known in the art and can be found in, for example, Maniatis, T., Fritsch, E. F., Sambrook, J. in Molecular Cloning: A Laboratory Manual, Second Edition, Cold Spring Harbor Laboratory Press, Cold Spring Harbor, N.Y. 1989.

It is readily apparent to those skilled in the art that other types of libraries, as well as libraries constructed from other cells or cell types, may be useful for isolating human calcium channel alpha1G-c-encoding DNA. Other types of libraries include, but are not limited to, cDNA libraries derived from other cells and genomic DNA libraries that include YAC (yeast artificial chromosome) and cosmid libraries.

It is readily apparent to those skilled in the art that suitable cDNA libraries may be prepared from cells or cell lines which have human calcium channel alpha1G-c activity. The selection of cells or cell lines for use in preparing a cDNA library to isolate human calcium channel alpha1G-c cDNA may be done by first measuring cell associated human calcium channel alpha1G-c activity using the measurement of calcium regulated biological activity.

Preparation of cDNA libraries can be performed by standard techniques well known in the art. Well known cDNA library construction techniques can be found for example, in Maniatis, T., Fritsch, E. F., Sambrook, J., Molecular Cloning: A Laboratory Manual, Second Edition (Cold Spring Harbor A Laboratory, Cold Spring Harbor, N.Y., 1989).

It is also readily apparent to those skilled in the art that DNA encoding human calcium channel alpha1G-c may also be isolated from a suitable genomic DNA library. Construction of genomic DNA libraries can be performed by standard techniques well known in the art. Well known genomic DNA library construction techniques can be found in Maniatis, T., Fritsch, E. F., Sambrook, J. in Molecular Cloning: A Laboratory Manual, Second Edition (Cold Spring Harbor Laboratory, Cold Spring Harbor, N.Y., 1989).

In order to clone the human calcium channel alpha1G-c gene by the above methods, the amino acid sequence of human calcium channel alpha1G-c may be necessary. To accomplish this, human calcium channel alpha1G-c protein may be purified and partial amino acid sequence determined by automated sequencers. It is not necessary to determine the entire amino acid sequence, but the linear sequence of two regions of 6 to 8 amino acids from the protein is determined for the production of primers for PCR amplification of a partial human calcium channel alpha1G-c DNA fragment.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the human calcium channel alpha1G-c sequence but will be capable of hybridizing to human calcium channel alpha1G-c DNA even in the presence of DNA oligonucleotides with mismatches. The mismatched DNA oligonucleotides may still sufficiently hybridize to the human calcium channel alpha1G-c DNA to permit identification and isolation of human calcium channel alpha1G-c encoding DNA. DNA isolated by these methods can be used to screen DNA libraries from a variety of cell types, from invertebrate and vertebrate sources, and to isolate homologous genes.

Purified biologically active human calcium channel alpha1G-c may have several different physical forms. Human calcium channel alpha1G-c may exist as a full-length nascent or unprocessed polypeptide, or as partially processed polypeptides or combinations of processed polypeptides. The full-length nascent human calcium channel alpha1G-c polypeptide may be posttranslationally modified by specific proteolytic cleavage events, which result in the formation of fragments of the full-length nascent polypeptide. A fragment, or physical association of fragments may have the full biological activity associated with human calcium channel alpha1G-c, however, the degree of human calcium channel alpha1G-c activity may vary between individual human calcium channel alpha1G-c fragments and physically associated human calcium channel alpha1G-c polypeptide fragments.

The cloned human calcium channel alpha1G-c DNA obtained through the methods described herein may be recombinantly expressed by molecular cloning into an expression vector containing a suitable promoter and other appropriate transcription regulatory elements, and transferred into prokaryotic or eukaryotic host cells to produce recombinant human calcium channel alpha1G-c protein. Techniques for such manipulations are fully described in Maniatis, T. et al., supra, and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria including E. coli, blue-green algae, plant cells, insect cells, fungal cells including yeast cells, and animal cells.

Specifically designed vectors allow the shuttling of DNA between hosts such as bacteria-yeast or bacteria-animal cells or bacteria-fungal cells or bacteria-invertebrate cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one that causes mRNAs to be initiated at high frequency. Expression vectors may include, but are not limited to, cloning vectors, modified cloning vectors, specifically designed plasmids or viruses.

A variety of mammalian expression vectors may be used to express recombinant human calcium channel alpha1G-c in mammalian cells. Commercially available mammalian expression vectors which may be suitable for recombinant human calcium channel alpha1G-c expression, include but are not limited to, pMAMneo (Clontech), pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and IZD35 (ATCC 37565).

A variety of bacterial expression vectors may be used to express recombinant human calcium channel alpha1G-c in bacterial cells. Commercially available bacterial expression vectors which may be suitable for recombinant human calcium channel alpha1G-c expression include, but are not limited to pET vectors (Novagen) and pQE vectors (Qiagen).

A variety of fungal cell expression vectors may be used to express recombinant human calcium channel alpha1G-c in fungal cells such as yeast. Commercially available fungal cell expression vectors which may be suitable for recombinant human calcium channel alpha1G-c expression include but are not limited to pYES2 (InVitrogen) and Pichia expression vector (InVitrogen).

A variety of insect cell expression vectors may be used to express recombinant human calcium channel alpha1G-c in insect cells. Commercially available insect cell expression vectors that may be suitable for recombinant expression of human calcium channel alpha1G-c include but are not limited to pBlueBacII (InVitrogen).

DNA encoding human calcium channel alpha1G-c may be cloned into an expression vector for expression in a recombinant host cell. Recombinant host cells may be prokaryotic or eukaryotic, including but not limited to bacteria such as E. coli. fungal cells such as yeast, mammalian cells including but not limited to cell lines of human, bovine, porcine, monkey and rodent origin, and insect cells including but not limited to drosophila and silkworm derived cell lines. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171), L-cells, and HEK-293 (ATCC CRL1573).

The expression vector may be introduced into host cells via any one of a number of techniques including but not limited to transformation, transfection, protoplast fusion, lipofection, and electroporation. The expression vector-containing cells are clonally propagated and individually analyzed to determine whether they produce human calcium channel alpha1G-c protein. Identification of human calcium channel alpha1G-c expressing host cell clones may be done by several means, including but not limited to immunological reactivity with anti-human calcium channel alpha1G-c antibodies, and the presence of host cell-associated human calcium channel alpha1G-c activity.

Expression of human calcium channel alpha1G-c DNA may also be performed using in vitro produced synthetic mRNA. Synthetic mRNA or mRNA isolated from human calcium channel alpha1G-c producing cells can be efficiently translated in various cell-free systems, including but not limited to wheat germ extracts and reticulocyte extracts, as well as efficiently translated in cell based systems, including but not limited to microinjection into frog oocytes, with microinjection into frog oocytes being generally preferred.

To determine the human calcium channel alpha1G-c DNA sequence(s) that yields optimal levels of human calcium channel alpha1G-c activity and/or human calcium channel alpha1G-c protein, human calcium channel alpha1G-c DNA molecules including, but not limited to, the following can be constructed: the full-length open reading frame of the human calcium channel alpha1G-c cDNA encoding the approximately 252 kDa protein from approximately base 1 to approximately base 6822 (these numbers correspond to first nucleotide of first methionine and last nucleotide before the first stop codon) and several constructs containing portions of the cDNA encoding human calcium channel alpha1G-c protein. All constructs can be designed to contain none, all or portions of the 5' or the 3' untranslated region of human calcium channel alpha1G-c cDNA. Human calcium channel alpha1G-c activity and levels of protein expression can be determined following the introduction, both singly and in combination, of these constructs into appropriate host cells. Following determination of the human calcium channel alpha1G-c DNA cassette yielding optimal expression in transient assays, this human calcium channel alpha1G-c DNA construct is transferred to a variety of expression vectors, for expression in host cells including, but not limited to, mammalian cells, baculovirus-infected insect cells, E. coli and the yeast S. cerevisiae.

Host cell transfectants and microinjected oocytes may be used to assay both the levels of human calcium channel alpha1G-c channel activity and levels of human calcium channel alpha1G-c protein by the following methods. In the case of recombinant host cells, this involves the co-transfection of one or possibly two or more plasmids, containing the human calcium channel alpha1G-c DNA encoding one or more fragments or subunits. In the case of oocytes, this involves the co-injection of synthetic RNAs for human calcium channel alpha1G-c protein. Following an appropriate period of time to allow for expression, cellular protein is metabolically labelled with, for example $^{35}$S-methionine for 24 hours, after which cell lysates and cell culture supernatants are harvested and subjected to immunoprecipitation with polyclonal antibodies directed against the human calcium channel alpha1G-c protein.

Other methods for detecting human calcium channel alpha1G-c activity involve the direct measurement of human calcium channel alpha1G-c activity in whole cells transfected with human calcium channel alpha1G-c cDNA or oocytes injected with human calcium channel alpha1G-c mRNA. Human calcium channel alpha1G-c activity is measured by biological characteristics of the host cells expressing human calcium channel alpha1G-c DNA. In the case of recombinant host cells expressing human calcium channel alpha1G-c patch voltage clamp techniques can be used to measure receptor activity and quantitate human calcium channel alpha1G-c protein. In the case of oocytes patch clamp as well as two-electrode voltage clamp techniques can be used to measure calcium channel alpha1G-c activity and quantitate human calcium channel alpha1G-c protein by determining single channel and whole cell conductances.

Levels of human calcium channel alpha1G-c protein in host cells are quantitated by immunoaffinity and/or ligand affinity techniques. Cells expressing human calcium channel alpha1G-c can be assayed for the number of human calcium channel alpha1G-c molecules expressed by measuring the amount of radioactive ligand binding to cell membranes. Human calcium channel alpha1G-c-specific affinity beads or human calcium channel alpha1G-c-specific antibodies are used to isolate for example $^{35}$S-methionine labelled or unlabelled human calcium channel alpha1G-c protein. Labelled human calcium channel alpha1G-c protein is analyzed by SDS-PAGE. Unlabelled human calcium channel alpha1G-c protein is detected by Western blotting, ELISA or RIA assays employing human calcium channel alpha1G-c specific antibodies.

Because the genetic code is degenerate, more than one codon may be used to encode a particular amino acid, and therefore, the amino acid sequence can be encoded by any of a set of similar DNA oligonucleotides. Only one member of the set will be identical to the human calcium channel alpha1G-c sequence but will be capable of hybridizing to human calcium channel alpha1G-c DNA even in the presence of DNA oligonucleotides with mismatches under appropriate conditions. Under alternate conditions, the mismatched DNA oligonucleotides may still hybridize to the human calcium channel alpha1G-c DNA to permit identification and isolation of human calcium channel alpha1G-c encoding DNA.

DNA encoding human calcium channel alpha1G-c from a particular organism may be used to isolate and purify homologues of human calcium channel alpha1G-c from other organisms. To accomplish this, the first human calcium channel alpha1G-c DNA may be mixed with a sample containing DNA encoding homologues of human calcium channel alpha1G-c under appropriate hybridization conditions. The hybridized DNA complex may be isolated and the DNA encoding the homologous DNA may be purified therefrom.

It is known that there is a substantial amount of redundancy in the various codons that code for specific amino acids. Therefore, this invention is also directed to those DNA sequences that contain alternative codons that code for the eventual translation of the identical amino acid. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide. Such substitutions are well known and are described, for instance in *Molecular Biology of the Gene*, 4$^{th}$ Ed. Bengamin Cummings Pub. Co. by Watson et al.

It is known that DNA sequences coding for a peptide may be altered so as to code for a peptide having properties that are different than those of the naturally occurring peptide. Methods of altering the DNA sequences include, but are not limited to site directed mutagenesis. Examples of altered properties include but are not limited to changes in the affinity of an enzyme for a substrate or a receptor for a ligand.

As used herein, a "functional derivative" of human calcium channel alpha1G-c is a compound that possesses a biological activity (either functional or structural) that is substantially similar to the biological activity of human calcium channel alpha1G-c. The term "functional derivatives" is intended to include the "fragments," "variants," "degenerate variants," "analogs" and "homologues" or to "chemical derivatives" of human calcium channel alpha1G-c. The term "fragment" is meant to refer to any polypeptide subset of human calcium channel alpha1G-c. The term "variant" is meant to refer to a molecule substantially similar in structure and function to either the entire human calcium channel alpha1G-c molecule or to a fragment thereof. A molecule is "substantially similar" to human calcium channel alpha1G-c if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical. The term "analog" refers to a molecule substantially similar in function to either the entire human calcium channel alpha1G-c molecule or to a fragment thereof. The term "functional" with respect to a calcium channel activity means that the channel is able to provide for and regulate entry of calcium channel selective ions, including, but not limited to Ca+2 or Ba+2 or ions that block the flow of Ca+2 or Ba+2, in response to a stimulus and/or bind ligands with affinity for the channel. Preferably such channel activity is distinguishable, such as by electrophysiological, pharmacological and other means known to those of skill in the art, from any endogenous calcium channel activity that is in the host cell.

Following expression of human calcium channel alpha1G-c in a recombinant host cell, human calcium channel alpha1G-c protein may be recovered to provide human calcium channel alpha1G-c in active form. Several human calcium channel alpha1G-c purification procedures are available and suitable for use. As described above for purification of human calcium channel alpha1G-c from natural sources, recombinant human calcium channel alpha1G-c may be purified from cell lysates and extracts, or from conditioned culture medium, by various combinations of, or individual application of salt fractionation, ion exchange chromatography, size exclusion chromatography, hydroxylapatite adsorption chromatography and hydrophobic interaction chromatography.

In addition, recombinant human calcium channel alpha1G-c can be separated from other cellular proteins by use of an immunoaffinity column made with monoclonal or polyclonal antibodies specific for full length nascent human calcium channel alpha1G-c, polypeptide fragments of human calcium channel alpha1G-c or human calcium channel alpha1G-c subunits.

Monospecific antibodies to human calcium channel alpha1G-c are purified from mammalian antisera containing antibodies reactive against human calcium channel alpha1G-c or are prepared as monoclonal antibodies reactive with human calcium channel alpha1G-c using the technique of Kohler and Milstein, *Nature* 256: 495–497 (1975). Monospecific antibody as used herein is defined as a single antibody species or multiple antibody species with homogenous binding characteristics for human calcium channel alpha1G-c. Homogenous binding as used herein refers to the ability of the antibody species to bind to a specific antigen or epitope, such as those associated with the human calcium channel alpha1G-c, as described above. Human calcium channel alpha1G-c specific antibodies are raised by immunizing animals such as mice, rats, guinea pigs, rabbits, goats, horses and the like, with rabbits being preferred, with an appropriate concentration of human calcium channel alpha1G-c either with or without an immune adjuvant.

Preimmune serum is collected prior to the first immunization. Each animal receives between about 0.1 mg and about 1000 mg of human calcium channel alpha1G-c associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of human calcium channel alpha1G-c in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the antigen in Freund's incomplete adjuvant by the same route. Booster injections are given at about three-week intervals until maximal titers are obtained. At about 7 days after each booster immunization or about weekly after a single immunization, the animals are bled, the serum collected, and aliquots are stored at about −20° C.

Monoclonal antibodies (mAb) reactive with human calcium channel alpha1G-c are prepared by immunizing inbred mice, preferably Balb/c, with human calcium channel alpha1G-c. The mice are immunized by the IP or SC route with about 0.1 mg to about 10 mg, preferably about 1 mg, of human calcium channel alpha1G-c in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 0.1 to about 10 mg of human calcium channel alpha1G-c in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions that will allow the formation of stable hybridomas. Fusion partners may include, but are not limited to: mouse myelomas P3/NS1/Ag4-1; MPC-11; S-194 and Sp 2/0, with Sp 2/0 being generally preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using human calcium channel alpha1G-c as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

Monoclonal antibodies are produced in vivo by injection of pristane primed Balb/c mice, approximately 0.5 ml per mouse, with about $2 \times 10^6$ to about $6 \times 10^6$ hybridoma cells about 4 days after priming. Ascites fluid is collected at approximately 8–12 days after cell transfer and the monoclonal antibodies are purified by techniques known in the art.

In vitro production of anti-human calcium channel alpha1G-c mAb is carried out by growing the hybridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of human calcium channel alpha1G-c in body fluids or tissue and cell extracts.

It is readily apparent to those skilled in the art that the above described methods for producing monospecific antibodies may be utilized to produce antibodies specific for human calcium channel alpha1G-c polypeptide fragments, or full-length nascent human calcium channel alpha1G-c polypeptide, or the individual human calcium channel alpha1G-c domains. Specifically, it is readily apparent to those skilled in the art that monospecific antibodies may be generated which are specific for human calcium channel alpha1G-c by immunizing an animal with an antigenic peptide derived from the 23 amino acid insert, or fragments thereof.

Human calcium channel alpha1G-c antibody affinity columns are made by adding the antibodies to Affigel-10 (Bio-Rad), a gel support which is activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) and the cell culture supernatants or cell extracts containing human calcium channel alpha1G-c or human calcium channel alpha1G-c subunits are slowly passed through the column. The column is then washed with phosphate buffered saline until the optical density ($A_{280}$) falls to background, then the protein is eluted with 0.23 M glycine-HCl (pH 2.6). The purified human calcium channel alpha1G-c protein is then dialyzed against phosphate buffered saline.

DNA clones, termed human calcium channel alpha1G-c, are identified which encode proteins that, when expressed in a recombinant host cell, form channels that regulate calcium influx and are sensitive to NPPB (5-Nitro-2-(3-phenylpropylamino)benzoic acid). The expression of human calcium channel alpha1G-c DNA results in the reconstitution of the properties observed in oocytes injected with human calcium channel alpha1G-c-encoding poly $(A)^+$ RNA, including direct activation with the appropriate stimuli.

The present invention is also directed to methods for screening for compounds that modulate the expression of DNA or RNA encoding human calcium channel alpha1G-c as well as the quantity of expressed human calcium channel alpha1G-c protein. The term "compound" refers to small organic or inorganic molecules (including divalent ions), synthetic or natural amino acid polypeptides, proteins, or synthetic or natural nucleic acid sequences. Compounds may modulate by increasing or attenuating the expression of DNA or RNA encoding human calcium channel alpha1G-c, or the quantity of cell surface human calcium channel alpha1G-c protein. Compounds that modulate the expression of DNA or RNA encoding human calcium channel alpha1G-c or the quantity of human calcium channel alpha1G-c protein may be detected by a variety of assays. Assays to measure changes in the level of expression of alpha1G-c can be accomplished by various means, well known in the art, for example changes in the quantity of mRNA, intracellular protein (newly synthesize protein being processed within the endoplasmic reticulum or Golgi apparatus), or cell surface protein. Levels of mRNA are detected by reverse transcription polymerase chain reaction (RT-PCR) or by differential gene expression (quantitative gene chips). Immunoaffinity quantitates levels of protein both within and on the surface of host cells. Protein-specific affinity beads or specific antibodies are used to isolate for example $^{35}$S-methionine labelled or unlabelled protein. Labelled protein is analyzed by SDS-PAGE. Unlabelled protein is detected by Western blotting, cell surface detection by fluorescent cell sorting, ELISA or RIA employing specific antibodies.

Assays that use eukaryotic cells for identifying compounds that modulate human alpha1G-c calcium channel activity are also provided. In practicing these assays the eukaryotic cell that expresses the heterologous human alpha1G-c calcium channel encoded by a DNA sequence described herein, is in a solution containing a test compound and a calcium channel selective ion, the cell membrane is depolarized, and current flowing into the cell is detected. If the test compound is one that modulates calcium channel activity, the current that is detected is different from that produced by depolarizing the same or a substantially identical cell in the presence of the same calcium channel-selective ion but in the absence of the compound. In preferred embodiments, the cells are mammalian cells, most preferably HEK293 cells, or amphibian oocytes. The assay method comprises the steps of: (a) measuring the activity of the human alpha1G-c in a cell that expresses the human alpha1G-c calcium channel; (b) contacting a compound with the cell; and (c) monitoring changes in the cell. In these assays, an agonist would increase Ca influx with no elevated K depolarizing stimulus, in the presence of concentrations of K that normally are not enough to activate the channels or shift the voltage dependence of inactivation. In these assays, an antagonist would block Ca influx induced by elevated potassium. Assays that measure electrophysiological calcium channel function measure the amount or duration of Ca influx, for example by using Ca sensitive dyes such as Fluo-3 or radioactive ions such as $^{45}$Ca or voltage clamp techniques. Voltage sensitive dyes and current clamp electrophysiological techniques can be used to measure depolarizations resulting from Ca influx. Yet another embodiment of the test method measures "downstream" effects of Ca influx by using a transcription based assay under inducible control of a Ca sensitive promotor, as described in PCT International Patent Application No. PCT/US91/5625, filed Aug. 7, 1991.

These assays may be a simple "yes/no" assays to determine whether there is a change in expression or function or they may be made quantitative by comparing the expression or function of a test sample with the levels of expression or function in a standard sample. Modulators identified any of these processes are useful as therapeutic agents.

Modulators identified in the assays disclosed herein are useful candidates as therapeutic agents for the treatment disorders that are mediated by human alpha1G-c activity. Such activities that may be mediated by human alpha1G-c include, epilepsy, schizophrenia, depression, sleep disorders, stress, endocrine disorders, respiratory disorder, peripheral muscle disorders, muscle excitability, Cushing's disease, fertilization, contraception, disorders involving neuronal firing regulation, respiratory disorders, hypertension, cardiac rhythm, potentiation of synaptic signals, improving arterial compliance in systolic hypertension, vascular tone such as by decreasing vascular swelling, cardiac hypertrophy, cardiac fibrosis, atherosclerosis, cardiovascular disorders, including but not limited to: myocardial infarct, cardiac arrhythmia, heart failure and angina pectoris, and cellular growth (protein synthesis, cell differentiation, and proliferation). The compounds that modulate human alpha1G-c calcium channel activity may be useful in regulating vascular smooth muscle tone, either vasodilating or vasoconstricting in: (a) treatments for reestablishing blood pressure control, e.g., following traumatic injury, surgery or cardiopulmonary bypass, and in prophylactic treatments designed to minimize cardiovascular effects of anaesthetic drugs; (b) treatments for improving vascular reflexes and blood pressure control by the autonomic nervous system. The compounds that modulate human alpha1G-c calcium channel activity may also be useful in treatments of urological disorders and reproductive disorders: (a) treating and restoring renal function following surgery, traumatic. injury, uremia and adverse drug reactions; (b) treating bladder dysfunctions; and (c) uremic neuronal toxicity and hypotension in patients on hemodialysis; reproductive disorders; (d) disorders of sexual function including impotence; (e) alcoholic impotence (under autonomic control that may be subject to T-type calcium channel controls); and (f) fertility (via direct action upon Sertoli cells (in males) or the zona pecullicda (for mammalian eggs) or by modulation of hormonal feedback). The compounds that modulate human alpha1G-c calcium channel activity may be useful in treatments of hepatic disorders in treating and reducing neuronal toxicity and autonomic nervous system damage resulting from acute overconsumption of alcohol. The compounds that modulate human alpha1G-c calcium channel activity may be useful treatments for neurologic disorders; (a) epilepsy and diencephalic epilepsy; (b) Parkinson's disease; and (c) aberrant temperature control, such as, abnormalities of shivering and sweat gland secretion and peripheral vascular blood supply. The compounds that modulate human alpha1G-c calcium channel activity may be useful for treating abnormal respiration, e.g., post-surgical complications of anesthetics and endocrine disorders; (a) aberrant pituitary and hypothalamic functions including abnormal secretion of noradrenaline, dopamine and other hormones; and (b) treatments for overproduction of insulin, thyroxine adrenaline and other hormonal imbalances.

Kits containing human calcium channel alpha1G-c DNA or RNA, antibodies to human calcium channel alpha1G-c, or human calcium channel alpha1G-c protein may be prepared. Such kits are used to detect DNA that hybridizes to human calcium channel alpha1G-c DNA or to detect the presence of human calcium channel alpha1G-c protein or peptide fragments in a sample. Such characterization is useful for a variety of purposes including but not limited to forensic analyses, diagnostic applications, and epidemiological studies.

The DNA molecules, RNA molecules, recombinant protein and antibodies of the present invention may be used to screen and measure levels of human calcium channel alpha1G-c DNA, human calcium channel alpha1G-c RNA or human calcium channel alpha1G-c protein. The recombinant proteins, DNA molecules, RNA molecules and antibodies lend themselves to the formulation of kits suitable for the detection and typing of human calcium channel alpha1G-c. Such a kit would comprise a compartmentalized carrier suitable to hold in close confinement at least one container. The carrier would further comprise reagents such as recombinant human calcium channel alpha1G-c protein or anti-human calcium channel alpha1G-c antibodies suitable for detecting human calcium channel alpha1G-c. The carrier may also contain a means for detection such as labeled antigen or enzyme substrates or the like.

Nucleotide sequences that are complementary to the human calcium channel alpha1G-c encoding DNA sequence can be synthesized for antisense therapy. These antisense molecules may be DNA, stable derivatives of DNA such as phosphorothioates or methylphosphonates, RNA, stable derivatives of RNA such as 2'-O-alkylRNA, or other human calcium channel alpha1G-c antisense oligonucleotide mimetics. Human calcium channel alpha1G-c antisense molecules may be introduced into cells by microinjection, liposome encapsulation or by expression from vectors harboring the antisense sequence. Human calcium channel alpha1G-c antisense therapy may be particularly useful for the treatment of diseases where it is beneficial to reduce human calcium channel alpha1G-c activity.

Human calcium channel alpha1G-c gene therapy may be used to introduce human calcium channel alpha1G-c into the cells of target organisms. The human calcium channel alpha1G-c gene can be ligated into viral vectors that mediate transfer of the human calcium channel alpha1G-c DNA by infection of recipient host cells. Suitable viral vectors include retrovirus, adenovirus, adeno-associated virus, herpes virus, vaccinia virus, polio virus and the like. Alternatively, human calcium channel alpha1G-c DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo as well as in vivo human calcium channel alpha1G-c gene therapy. Human calcium channel alpha1G-c gene therapy may be particularly useful for the treatment of diseases where it is beneficial to elevate human calcium channel alpha1G-c activity.

Pharmaceutically useful compositions comprising human calcium channel alpha1G-c DNA, human calcium channel alpha1G-c RNA, or human calcium channel alpha1G-c protein, or modulators of human calcium channel alpha1G-c activity, may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, or modulator.

Therapeutic or diagnostic compositions of the invention are administered to an individual in amounts sufficient to treat or diagnose disorders in which modulation of human calcium channel alpha1G-c-related activity is indicated. The effective amount may vary according to a variety of factors such as the individual's condition, weight, sex and age. Other factors include the mode of administration. The pharmaceutical compositions may be provided to the individual by a variety of routes such as subcutaneous, topical, oral and intramuscular.

The term "chemical derivative" describes a molecule that contains additional chemical moieties that are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages defined by routine testing in order to obtain optimal inhibition of the human calcium channel alpha1G-c or its activity while minimizing any potential toxicity. In addition, co-administration or sequential administration of other agents may be desirable.

The present invention also has the objective of providing suitable topical, oral, systemic and parenteral pharmaceutical formulations for use in the novel methods of treatment of the present invention. The compositions containing compounds or modulators identified according to this invention as the active ingredient for use in the modulation of human calcium channel alpha1G-c receptors can be administered in a wide variety of therapeutic dosage forms in conventional vehicles for administration. For example, the compounds or modulators can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a human calcium channel alpha1G-c modulating agent.

The daily dosage of the products may be varied over a wide range from 0.01 to 1,000 mg per patient, per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. The dosages of the human calcium channel alpha1G-c modulators are adjusted when combined to achieve desired effects. On the other hand, dosages of these various agents may be independently optimized and combined to achieve a synergistic result wherein the pathology is reduced more than it would be if either agent were used alone.

Advantageously, compounds or modulators of the present invention may be administered in a single daily dose, or the total daily dosage may be administered in divided doses of two, three or four times daily. Furthermore, compounds or modulators for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds or modulators of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds or modulators herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents that may be employed include glycerin and the like. For parenteral administration, sterile suspensions and solutions are desired. Isotonic preparations, which generally contain suitable preservatives, are employed when intravenous administration is desired.

Topical preparations containing the active drug component can be admixed with a variety of carrier materials well known in the art, such as, eg., alcohols, aloe vera gel, allantoin, glycerine, vitamin A and E oils, mineral oil, PPG2 myristyl propionate, and the like, to form, eg., alcoholic solutions, topical cleansers, cleansing creams, skin gels, skin lotions, and shampoos in cream or gel formulations.

The compounds or modulators of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds or modulators of the present invention may also be coupled with soluble polymers as targetable drug carriers. Such polymers can include polyvinyl-pyrrolidone, pyran copolymer, polyhydroxypropylmethacryl-amidephenol, polyhydroxy-ethylaspartamidephenol, or polyethyleneoxidepolylysine substituted with palmitoyl residues. Furthermore, the compounds or modulators of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

For oral administration, the compounds or modulators may be administered in capsule, tablet, or bolus form or alternatively they can be mixed in the animals feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, and/or binders such that a uniform mixture is obtained. An inert ingredient is one that will not react with the compounds or modulators and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5% by weight of the active ingredient.

The compounds or modulators may alternatively be administered parenterally via injection of a formulation consisting of the active ingredient dissolved in an inert liquid carrier. Injection may be either intramuscular, intraluminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the compounds or modulators is possible through the use of a liquid drench or a shampoo containing the instant compounds or modulators as an aqueous solution or suspension. These formulations generally contain a suspending agent such as bentonite and normally will also contain an antifoaming agent. Formulations containing from 0.005 to 10% by weight of the active ingredient are acceptable. Preferred formulations are those containing from 0.01 to 5% by weight of the instant compounds or modulators.

The following examples illustrate the present invention without, however, limiting the same thereto.

EXAMPLE 1

Generation of a Human Thalamus Library cDNA Synthesis

First Strand Synthesis

Approximately 5 $\mu$g of human thalamus mRNA (Clontech) was used to synthesize cDNA using the cDNA synthesis kit (Life Technologies). Two microliters of Not1 primer adapter was added to 5 $\mu$l of mRNA and the mixture was heated to 70° C. for 10 minutes and placed on ice. The following reagents were added on ice: 4 $\mu$l of 5× first strand buffer (250 mM TRIS-HCl (pH8.3), 375 mM KCl, 15 mM $MgCl_2$), 2 $\mu$l of 0.1M DTT, 10 mM dNTP (nucleotide triphosphates) mix and 1 $\mu$l of DEPC treated water. The reaction was incubated at 42° C. for 5 minutes. Finally, 5 $\mu$l of Superscript RT II was added and incubated at 42° C. for 2 more hours. The reaction was terminated on ice.

Second Strand Synthesis

The first strand product was adjusted to 93 $\mu$l with water and the following reagents were added on ice: 30 $\mu$l of 5× 2nd strand buffer (5×concentration (in mM): 100 mM TRIS-HCl (pH6.9), 450 mM KCl, 23 mM $MgCl_2$, 0.75 mM β-NAD+, 50 mM $(NH_4)_2SO_4$), 3 $\mu$l of 10 mM dNTP (nucleotide triphosphates), 1 $\mu$l E. coli DNA ligase (10 units )1 $\mu$l RNase H (2 units), 4 $\mu$l DNA pol I (10 units)). The reaction was incubated at 16° C. for 2 hours. The DNA from second strand synthesis was treated with T4 DNA polymerase and placed at 16° C. to blunt the DNA ends. The double stranded cDNA was extracted with 150 $\mu$l of a mixture of phenol and chloroform (1:1, v:v) and precipitated with 0.5 volumes of 7.5 M NH4OAc and 2 volumes of absolute ethanol. The pellet was washed with 70% ethanol and dried down at 37° C. to remove the residual ethanol. The double stranded DNA pellet was resuspended in 25 $\mu$l of water and the following reagents were added; 10 $\mu$l of 5×T4 DNA ligase buffer, 10 $\mu$l of Sal1 adapters and 5 $\mu$l of T4 DNA ligase. The ingredients were mixed gently and ligated overnight at 16° C. The ligation mix was extracted with phenol:chloroform:isoamyl alcohol, vortexed thoroughly and centrifuged at room temperature for 5 minutes at 14,000×g to separate the phases. The aqueous phase was transferred to a new tube and the volume adjusted to 100 ml with water. The purified DNA was size selected on a chromaspin 1000 column (Clontech) to eliminate the smaller cDNA molecules. The double stranded DNA was digested with NotI restriction enzyme for 3–4 hours at 37° C. The restriction digest was electrophoresed on a 0.8% low melt agarose gel. The cDNA in the range of 1–5 kb was cut out and purified using Gelzyme (Invitrogen). The product was extracted with phenol:chloroform and precipitated with $NH_4OAc$ and absolute ethanol. The pellet was washed with 70% ethanol and resuspended in 10 ml of water.

Ligation of cDNA to the Vector

The cDNA was split up into 5 tubes (2 μl each) and the ligation reactions were set up by adding 4.5 μl of water, 2 μl of 5×ligation buffer, 1 μl of p-Sport vector DNA (cut with Sal-1/Not1 and phosphatase treated) and 0.5 μl of T4 DNA ligase. The ligation was incubated at 40° C. overnight.

Introduction of Ligated cDNA into E.coli by Electroporation

The ligation reaction volume was adjusted to a total volume of 20 μl with water. Five milliliters of yeast tRNA, 12.5 ml of 7.5M $NH_4OAc$ and 70 ml of absolute ethanol (−20° C.) was added. The mixture was vortexed thoroughly, and immediately centrifuged at room temperature for 20 minutes at 14000×g. The pellets were washed in 70% ethanol and each pellet was resuspended in 5 ml of water. All 5 ligations (25 ml) were pooled and 100 μl of DH10B electro-competent cells (Life Technologies) were electroporated with 1 ml of DNA (total of 20 electroporations), then plated out on ampicillin plates to determine the number of recombinants (cfu) per microliter. The entire library was seeded into 2 liters of Super Broth and maxipreps were made using Promega Maxi Prep kit and purified on cesium chloride gradients.

EXAMPLE 2

Library Screening/Human Calcium Channel Alpha1G-c Generation

Human Thalamus Library Screening

One microliter aliquots of the human thalamus library were electroporated into Electromax DH10B cells (Life Technologies). The volume was adjusted to 1 ml with SOC media and incubated for 60 minutes at 37° C. with shaking. The library was then plated out on 150 cm² plates containing LB to a density of 20000 colonies per plate. These cultures were grown overnight at 37° C.

A human calcium channel alpha1G-c probe was generated by polymerase chain reaction using the following primer pair:

SEQ.ID.NO.:1 5' oligo (18341F) 5' GCACTGCCAGTGGC-CGAGGG

SEQ.IN.NO.:2 3' oligo (18747R): 5'_CCATGGCGATGGTGATGCAG

The probe was generated by PCR using regular PCR conditions using 5' and 3' probe oligos (bOOng each) and 10 ng of diluted miniprep DNA. The resulting 274 bp fragment was run on 1% agarose gel and purified using GENECLEAN kit (Bio 101, Inc.). About 100 ng of the purified probe was labeled with alpha 32P using oligolabeling kit from Pharmacia and the labeled DNA was purified with S-200 columns (Pharmacia).

The library colonies were lifted on Protran nitrocellulose filters (Scheicher & Schuel) and the DNA was denatured in 1.5 M NaCl, 0.5 M NaOH. The filter disks were neutralized with 1.5 M NaCl, 0.5 M Tris-HCl, pH 7.5 and then UV crosslinked to the membrane using a UV-Stratalinker (Stratagene). The filters were washed several times in wash solution (50 mM Tris-HCl, pH 8.0; 1 M NaCl; 1 mM EDTA; 0.1% SDS) at room temperature. Then the disks were incubated in 1×southern pre-hybridization buffer (5'-3' Inc) containing 50% formarnide and 100 ug/ml of sheared salmon sperm DNA (5'-3' Inc) for 6 hours at 42 C. Finally, hybridization was performed overnight at 42 C. in 1×hybridization buffer (5'-3') containing 50% formamide, 100 ng of sheared salmon sperm DNA in the presence of labeled probe ($5\times10^5$ to $1\times10^6$ cpm/ml of hybridization buffer).

The disks were washed once in 2×SSC, 0.2% SDS at room temperature for 30 minutes, once in 0.2×SSC, 0.1%SDS at 50 C. for 30 minutes, once in 0.2×SSC, 0.1%SDS at 55 C. for 30 minutes and once in 0.2×SSC, 0.1% SDS at 60 C. for 15 minutes. The membranes were than placed on sheets of filter paper, wrapped in the Saran Wrap and exposed to the film at −20 C. overnight.

Positive clones were identified and collected by coring the colonies from the original plate. The colonies were incubated in 2 ml of LB for 2 hours at 37° C. Dilutions of the cultures were plated onto LB agar plates and the filter-lifting, hybridizing, washing, colony-picking procedure was repeated. Individual clones from the second screen were picked and digested with EcoRI/NotI to determine the size of the inserts, and the inserts were sequenced.

Three different clones between 3–5kb in length were identified with open reading frames. These were digested with $EcoR_1$/Xho1 and Xho1/Not1. These two pieces that were 4.2 kb and 3.2 kb were subjected to a 3 way ligation using an aliquot of pSport-1 vector that was cut with EcoR1 and Not1 and purified on a low melting point agarose gel. The ligated circular plasmid DNA was transformed into DH5 alpha bacterial cells from Gibco BRL. A few clones were picked and the entire 7.4 kb sequence was reconfirmed. A maxiprep of the plasmid DNA was obtained using the Promega kit. This DNA was further digested with EcoR1 and Not 1 and the 7.4 kb was inserted into the expression vector pGEM HE . Large-scale preparation of DNA was done using a MEGA prep kit (Promega.).

EXAMPLE 3

Cloning Human Calcium Channel Alpha1G-c cDNA into a Mammalian Expression Vector

The human calcium channel alpha1G-c cDNAs (collectively referred to as hCaChalpha1G-c) were cloned into the mammalian expression vector pcDNA3.1/Zeo(+). The plasmid DNA in p-Sport vector was digested with Not I and EcoR1 (NEB) to create cohesive ends. The product was purified by a low melting agarose gel electrophoresis. The pcDNA3.1/Zeo(+) vector was digested with EcoR1 and Not1 enzymes and subsequently purified on a low melt agarose gel. The linear vector was used to ligate to the human calcium channel alpha1G-c cDNA inserts.

EXAMPLE 4

Construction of a Stable Cell Line Expressing the Human Alpha1G-c

Recombinants were isolated, designated human calcium channel alpha1G-c, and are used to transfect mammalian cells (HEK293, COS-7 or CHO-K1 cells) using the Effectene non-liposomal lipid based transfection kit (Quiagen). Stable cell clones are selected by growth in the presence of zeocin. Single zeocin resistant clones are isolated and shown to contain the intact human calcium channel alpha1G-c gene. Clones containing the human calcium channel alpha1G-c cDNAs are analyzed for human calcium channel alpha1G-cprotein expression. Recombinant plasmids containing human calcium channel alpha1G-c encoding DNA are used to transform the mammalian COS or CHO cells or HEK293 cells.

Cells expressing human calcium channel alpha1G-c, stably or transiently, are used to test for expression of human calcium channel alpha1G-c activity. These cells are used to identify and examine other compounds for their ability to modulate, inhibit or activate the human calcium channel alpha1G-c.

Cassettes containing the human calcium channel alpha1G-c cDNA in the positive orientation with respect to the promoter are ligated into appropriate restriction sites 3' of the promoter and identified by restriction site mapping and/or sequencing. These cDNA expression vectors are introduced into fibroblastic host cells for example COS-7 (ATCC# CRL1651), and CV-1 tat [Sackevitz et al., Science 238: 1575 (1987)], 293, L (ATCC# CRL6362)] by standard methods including but not limited to electroporation, or chemical procedures (cationic liposomes, DEAE dextran, calcium phosphate). Transfected cells and cell culture supernatants are harvested and analyzed for human calcium channel alpha1G-c expression as described herein.

All of the vectors used for mammalian transient expression can be used to establish stable cell lines expressing human calcium channel alpha1G-c. Unaltered human calcium channel alpha1G-c receptor cDNA constructs cloned into expression vectors are expected to program host cells to make human calcium channel alpha1G-c protein. The transfection host cells include, but are not limited to, CV-1-P [Sackevitz et al., Science 238: 1575 (1987)], tk-L [Wigler, et al. Cell 11: 223 (1977)], NS/0, and dHFr- CHO [Kaufmnan and Sharp, J. Mol. Biol. 159: 601, (1982)].

Human calcium channel alpha1G-c cDNA constructs are also ligated into vectors containing amplifiable drug-resistance markers for the production of mammalian cell clones synthesizing the highest possible levels of human calcium channel alpha1G-c. Following introduction of these constructs into cells, clones containing the plasmid are selected with the appropriate agent, and isolation of an over-expressing clone with a high copy number of plasmids is accomplished by selection in increasing doses of the agent.

Co-transfection of any vector containing human calcium channel alpha1G-c cDNA with a drug selection plasmid including, but not limited to G418, aminoglycoside phosphotransferase; hygromycin, hygromycin-B phospholransferase; APRT, xanthine-guanine phosphoribosyl-transferase or zeocin, will allow for the selection of stably transfected clones. Levels of human calcium channel alpha1G-c are quantitated by the assays described herein (EXAMPLE 6).

The expression of recombinant human calcium channel alpha1G-c is achieved by transfection of full-length human calcium channel alpha1G-c cDNA into a mammalian host cell.

EXAMPLE 5

Characterization of Functional Protein Encoded by pCaChalpha1G-c in Xenopus Oocytes

*Xenopus laevis* oocytes were prepared and injected using standard methods previously described and known in the art (Fraser, S. P. et al. (1993)). Ovarian lobes from adult female *Xenopus laevis* (Nasco, Fort Atkinson, Wis.) were teased apart, rinsed several times in nominally Ca-free saline containing: 82.5 mM NaCl, 2.5 mM KCl, 1 mM $MgCl_2$, 5 mM HEPES, adjusted to pH 7.0 with NaOH (OR-2), and gently shaken in OR-2 containing 0.2% collagenase Type 1 (ICN Biomedicals, Aurora, Ohio) for 2–5 hours. When approximately 50% of the follicular layers were removed, Stage V and VI oocytes were selected and rinsed in media consisting of 75% OR-2 and 25% ND-96. The ND-96 contained: 100 mM NaCl, 2 mM KCl, 1 mM $MgCl_2$, 1.8 mM $CaCl_2$, 5 mM HEPES, 2.5 mM Na pyruvate, gentamicin (50 ug/ml), adjusted to pH 7.0 with NaOH. The extracellular $Ca^{+2}$ was gradually increased and the cells were maintained in ND-96 for 2–24 hours before injection. For in vitro transcription, pGEM HE which had been modified to contain the multiple cloning site from pSPORT (Liman, E. R. et al. (1992)) containing human calcium channel alpha1G-c was linearized with NotI and transcribed with T7 RNA polymerase (Promega) in the presence of the cap analog m7G(5')ppp(5')G. The human alpha1G-c contained its natural Kozak sequence. The synthesized cRNA was precipitated with ammonium acetate and isopropanol, and resuspended in 50 µl nuclease-free water. cRNA was quantified using formaldehyde gels (1% agarose, 1×MOPS , 3% formaldehyde) against RNA markers (Gibco BRL, 0.24–9.5 Kb).

Oocytes were injected with 50 nl of the human calcium channel alpha1G-c cRNA (about 600 ng). Control oocytes were injected with 50 nl of water. Oocytes were incubated in ND-96 before analysis for expression of the human calcium channel alpha1G-c. Incubations and collagenase digestion were carried out at room temperature. Injected oocytes were maintained in 48 well cell culture clusters (Costar; Cambridge, Mass.) at 18° C. Whole cell agonist-induced currents were measured 3–6 days after injection with a conventional two-electrode voltage clamp (GeneClamp500, Axon Instruments, Foster City, Calif.) using standard methods previously described and known in the art (Dascal, N. (1987)). The microelectrodes were filled with 3 M KCl, which had resistances of 1 and 2 MΩ. Cells were continuously perfused with ND96 at 2–5 mi/min at room temperature unless indicated. In some experiments, cells were bathed in a 40 mM Ba saline containing (in mM): 40 $BaCl_2$, 2 KCl, 36 TEA-Cl, 5 4-AP and 5 HEPES, pH 7.6. Membrane voltage was clamped at –100 mV unless indicated.

Depolarizing voltage steps elicited inward currents in oocytes that had been injected with RNA transcribed from the cloned human calcium channel alpha1G-c cDNA as shown in FIGS. 4a,b. In some experiments in which oocytes expressed large outward currents and slowly activating inward currents at negative potentials (activation of endogenous Ca-activated Cl currents), oocytes were bathed in 40 mM Ba saline. Due to effects of Ba2+ on surface charge screening (Wilson et al., 1983), we usually used more physiological conditions (2 mM extracellular $Ca^{2+}$; ND96).

FIG. 4a shows a representative family of current traces elicited by depolarizing pulses applied to the oocyte. Inward $Ba^{2+}$ currents activated slowly near threshold potentials and with larger depolarizing voltage pulses, the currents activated more quickly and inactivated, producing a signature "criss-cross" pattern for classical T-type currents (Randall and Tsien, 1997). Water-injected oocytes had no detectable inward currents. Peak currents recorded in 2 mM extracellular $Ca^{2+}$ were –380+/–170 nA (n=9), similar to that observed with $Ba^{2+}$ as the charge carrier (–240+/–20 nA; n=8). The threshold voltage recorded in ND96 was about –59 mV (n=9). The voltage that elicited maximal currents was –29+/–5 mV (n=9). The voltage at which currents reversed sign was +29+/–5 mV (n=4). The time to peak from the onset of the voltage pulse was 5.2+/–2 msec (n=9). In 40 mM $Ba^{2+}$ solution, the voltage dependence of activation was shifted slightly along the voltage axis (Huguenard, 1996; Perez-Reyes et al., 1998). The voltage eliciting peak currents was –33+/–2 mV (n=8). The time to peak response was similar to that recorded in 2 mM $Ca^{2+}$ (4.8+/–0.3 msec).

Steady state inactivation (FIGS. 4c,d) was studied by applying 4 sec long prepulses followed by a test pulse to –30 mV to measure channel availability. In some experiments a 5 msec repolarization pulse to −100 mV was performed to close any channels still open at the end of the 4 sec pulse. Results were similar and combined. Similar $V_{0.5}$ for inactivation for the cloned mouse alpha1G (AJ012569 contains the insert observed in the present invention in intracellular loop II-III as well as an extra 18 amino acid insert in intracellular loop between domains III–IV) expressed in HEK293 cells were obtained in $Ca^{2+}$ and $Ba^{2+}$ salines (Klugbauer et al., 1999). FIG. 4c shows representative current traces recorded during the test pulse. The percent of maximum response was calculated, plotted as a function of the prepulse potential and fit with a Boltzmann equation (FIG. 4d). Inactivation of human alpha1G-c occurred at sub-threshold voltages and displayed a steep voltage dependence (slope −4.9 [−6.0 to −3.8], n=7). The voltage dependence of inactivation occurred at −67 mV with 95% confidence interval of −68.3 to −65.8 mV (n=7 experiments; CaSOS). The voltage dependence of inactivation was similar when recorded in 40 mM $Ba^{2+}$ (−71+/−5 mV, n=5).

A defining feature of T-type calcium currents is that they deactivate relatively slowly compared to HVA calcium currents, producing slowly decaying tail currents after a depolarizing pulse. A 5 msec voltage step to −30 mV was followed by a step to −100 mV. The tau for current deactivation was 2.2+/−0.4 msec (n=3), similar to values reported for T-type currents.

Figure 5:
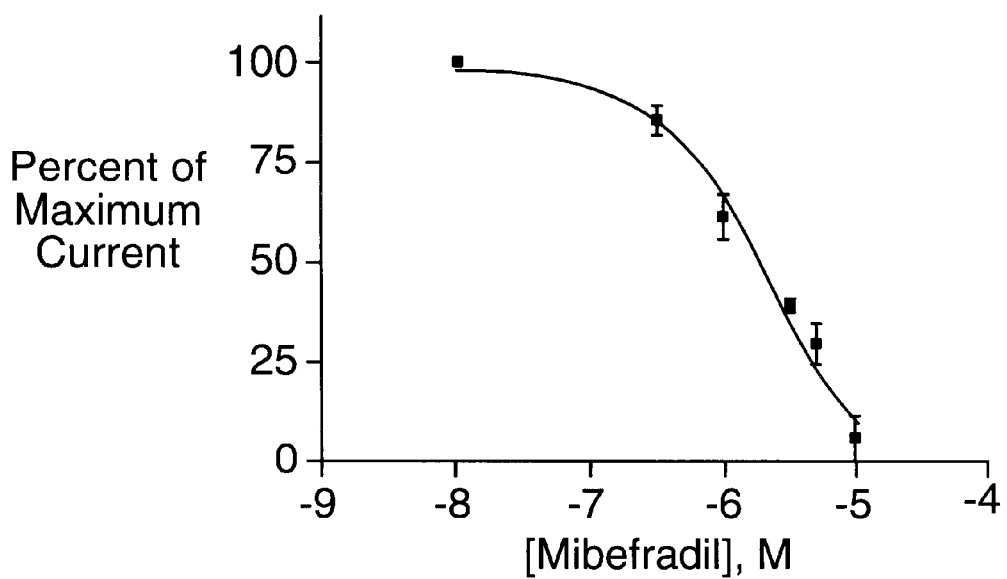
FIG. 5—Pharmacological characterization of human alpha1G-c expressed in Xenopus oocytes: dose dependent block by mibefradil. The responses to the indicated concentrations of mibefradil were bath applied to oocytes expressing human calcium channel alpha1G-c cRNA. Shown are 1–3 concentrations tested on 7 individual oocytes. The IC50 was 2.5 $\mu$M with a 95% confidence interval of 1.3 to 4.9 $\mu$M. Oocytes were bathed in ND96.

The pharmacological characterization of human alpha1G-c expressed in Xenopus oocytes was determined for mibefradil, $Ni^{2+}$, $Cd^{2+}$, amiloride and ethosuximide. The effect of the indicated concentrations of mibefradil on peak T-currents was determined. Mibefradil was bath applied to oocytes expressing human calcium channel alpha1G-c cRNA (FIG. 5). Shown are 1–3 concentrations tested on 7 individual oocytes. The $IC_{50}$ was 2.5 $\mu$M with a 95% confidence interval of 1.3 to 4.9 $\mu$M. Oocytes were bathed in ND96, The present invention was relatively insensitive to $Ni^{2+}$ blockade, similar to that observed for the rat alpha1G (AJ027984) (Perez-Reyes et al., 1998). 200 $\mu$M $NiCl_2$ blocked the peak current by 25+/−6% (n=3); in the same cell, 1 mM $NiCl_2$ blocked about twice the current blocked by 200 $\mu$M $Ni^{2+}$. Oocytes were voltage clamped at −100 mV between test pulses. $Cd^{2+}$ (100 $\mu$M) blocked T-currents by 44+/−9% (n=3).

The present invention was sensitive to amiloride block. 500 $\mu$M amiloride blocked peak currents by only 23+/−4% (n=4), similar to the block observed at rat spinal motoneurons (Huguenard, 1996). This concentration would completely block some T-type calcium currents (e.g., human alpha1H; see Background). Oocytes were maintained at −100 mV between voltage pulses and similar results were obtained for oocytes bathed in ND96 and $Ba^{2+}$ salines.

The present invention was sensitive to block by the antiepileptic ethosuximide. 600 $\mu$M ethosuximide (Sigma), within the range of therapeutically relevant concentrations for the treatment of absence epilepsy (see Background), reversibly blocked peak currents by 26+/−−3% (n=3). Oocytes were maintained at −100 mV between voltage pulses and similar results were obtained for oocytes bathed in ND96 and $Ba^{2+}$ salines. Human alpha1H currents are blocked only ~7% by 300 $\mu$M ethosuximide (WO 99/28342).

Interestingly, the chloride channel blocker NPPB (5-Nitro-2-(3-phenylpropylamino)benzoic acid) blocked human alpha1G-c currents expressed in oocytes. 20, 100 and 200 $\mu$M NPPB blocked 22+/−6% (n=3), 55+/−7% (n=3), and 89+/−7% (n=3), respectively. Another chloride channel blocker 9-AC (anthracene-9-carboxylic acid, Sigma) was less effective in blocking T-currents; 100 uM 9-AC blocked peak currents by 30+/−3% (n=4). DIDS (4,4'-diisothiocyanatostilbene-2.2'-disulfonic acid (Sigma); 100 $\mu$M) and niflumic acid (100 $\mu$M) had no effect on peak human alpha1G-c currents. DIDS and niflumic acid blocked the current by 16+/−13% (n=3) and 0+/−2% (n=3), respectively.

EXAMPLE 6

Characterization of Human Calcium Channel Alpha1G-c in Human HEK 293 Cell Line

Human HEK293 cells are transfected with human calcium channel alpha1G-c pCaChalpha1Gc (EXAMPLE 4). Transient transfections 1 $\mu$g of pCaChalpha1G per $10^6$ cells per 100 mm dish are performed using the Effectene tranfection kit (Quiagen; 301425). Three days after transfection, cells are plated onto 96-well plates (Biocoat, poly-D-lysine coated black/clear plate; Becton Dickinson part #354640). After one day, wells are rinsed with F12/DMEM, then incubated in Fluo-4 (2 $\mu$M) with Pluronic acid (20%, 40 $\mu$l used in 20 mls total volume) for 1 hour at room temperature. Plates are assayed using the FLIPR (Molecular Devices, FL-101). Cells are challenged with elevated K+ to achieve a final concentrations of 10, 25 and 43 mM $K^+$ (applied in 40 $\mu$L added to 80 $\mu$l at a velocity of 50 $\mu$l/sec). Transfections with vector alone are tested as controls. The basal buffer contains (in mM): 123 NaCl, 2 KCl, 1 $MgCl_2$, 2 $CaCl_2$, 15 glucose and 20 HEPES, pH 7.4.

Cells stably expressing the human alpha1G-c are plated onto 96-well plates (Biocoat, poly-D-lysine coated black/clear plate; Becton Dickinson part #354640) and grown to confluence. Wells are rinsed with F12/DMEM, then incubated in Fluo-4 (2 $\mu$M) with Pluronic acid (20%, 40 $\mu$l used in 20 mls total volume) for 1 hour at room temperature. Plates are assayed using the FLIPR (Molecular Devices, FL-101). Cells are challenged with elevated K+ (in 40 $\mu$l added to 80 $\mu$l at a velocity of 50 $\mu$l/sec).

The whole cell patch clamp technique (Hamill, O. P. et al. (1981)) is used to record ligand-induced currents from HEK293 stably expressing human calcium channel alpha1G-c maintained for >1 day on 12 mm coverslips. Cells are visualized using a Nikon Diaphot 300 with DIC Nomarski optics. Cells are continuously perfused in a physiological saline (~0.5 ml/min) unless otherwise indicated. The standard physiological saline ("CaCh physiological saline (CaChPS") contains: 15 mM BaCl2, 150 mM CholineCl, 1 mM MgCl2 and 10 mM HEPES (pH 7.3, 325 mOsm as measured using a Wescor 5500 vapor-pressure (Wescor, Inc., Logan, Utah). Recording electrodes are fabricated from borosilicate capillary tubing (R6; Garner Glass, Claremont, Calif.), the tips are coated with dental periphery wax (Miles Laboratories, South Bend, Ind.), and have resistances of 1–2 MΩ when containing intracellular saline: 135 mM CsCl, 10 mM EGTA, 1 mM $MgCl_2$, 10 mM HEPES (pH 7.4, with TEA-OH, 290 mOsm). Current and voltage signals are detected and filtered at 2 kHz with an Axopatch ID patch-clamp amplifier (Axon Instruments, Foster City, Calif.), digitally recorded with a DigiData 1200B laboratory interface (Axon Instruents), and PC compatible computer system and stored on magnetic disk for off-line analysis. Data acquisition and analysis are performed with PClamp software.

EXAMPLE 7

Pimgar Structure Of the Human Calcium Channel Alpha1G-c Protein

The nucleotide sequences of human calcium channel alpha1G-c revealed single large open reading frame of about 6819 base pairs encoding 2273 amino acids. The cDNAs have 5' and 3'-untranslated extensions of about 511 and about 397 nucleotides for human calcium channel alpha1G-c, respectively. The first in-frame methionine was designated as the initiation codon for an open reading frame that predicts a human calcium channel alpha1G-c protein with an estimated molecular mass ($M_r$) of about 251.8 kDa.

The predicted human calcium channel alpha1G-c protein was aligned with nucleotide and protein databases and found to be similar to the human alpha1G "a" isoform (accession #AF126966) with the exception that the sequence presented herein contains a 23 amino acid insert in the second intracellular loop between domains I and II. The insert contains a putative CKII phosphorylation site at S971. This 23 amino acid insert is 91 and 87% identical to the homologous sequence in rat (AF125161) and mouse (AJ012569), respectively. However, this insert is not present in another rat alpha1G isoform (AF027984) which is the ortholog to the present invention in regard to the remainder of the sequence. The putative casein kinase II phosphorylation site in this insert in the present invention is not conserved in rat or mouse.

There are 8, 23, 15 and 12 putative PKA (ie., R/K R/K x T/S), PKC (ie., S/T×K/R), casein kinase II (CKII; ie. S/T xx D/E) and MGCK (mammary gland casein kinase; ie., S×E) phosphorylation sites, respectively. There are 8 potential N-linked glycosylation sites. There are no putative tyrosine phosphorylation motifs (i.e., R/K x x x D x x Y) in predicted intracellular domains.

EXAMPLE 8

Cloning Human Calcium Channel Alpha1G-c cDNA into *E. coli* Expression Vectors

Recombinant human calcium channel alpha1G-c is produced in *E. coli* following the transfer of the human calcium channel alpha1G-c expression cassette into *E. coli* expression vectors, including but not limited to, the pET series (Novagen). The pET vectors place human calcium channel alpha1G-c expression under control of the tightly regulated bacteriophage T7 promoter. Following transfer of this construct into an *E. coli* host that contain a chromosomal copy of the T7 RNA polymerase gene driven by the inducible lac promoter, expression of human calcium channel alpha1G-c is induced when an appropriate lac substrate (IPTG) is added to the culture. The levels of expressed human calcium channel alpha1G-c are determined by the assays described herein.

The cDNA encoding the entire open reading frame for human calcium channel alpha1G-c is inserted into the NdeI site of pET [16]11a. Constructs in the positive orientation are identified by sequence analysis and used to transform the expression host strain BL21. Transformants are then used to inoculate cultures for the production of human calcium channel alpha1G-c protein. Cultures may be grown in M9 or ZB media, whose formulation is known to those skilled in the art. After growth to an $OD_{600}$=1.5, expression of human calcium channel alpha1G-c is induced with 1 mM IPTG for 3 hours at 37° C.

EXAMPLE 9

Cloning Human Calcium Channel Alpha1G-c cDNA into a Baculovirus Expression Vector for Expression in Insect Cells Baculovirus vectors, which are derived from the genome of the AcNPV virus, are designed to provide high level expression of cDNA in the Sf9 line of insect cells (ATCC CRL #1711). Recombinant baculoviruses expressing human calcium channel alpha1G-c cDNA is produced by the following standard methods (InVitrogen Maxbac Manual): the human calcium channel alpha1G-c cDNA constructs are ligated into the polyhedrin gene in a variety of baculovirus transfer vectors, including the pAC360 and the BlueBac vector (InVitrogen). Recombinant baculoviruses are generated by homologous recombination following co-transfection of the baculovirus transfer vector and linearized AcNPV genomic DNA [Kitts, P. A., Nuc. Acid. Res. 18: 5667 (1990)] into Sf9 cells. Recombinant pAC360 viruses are identified by the absence of inclusion bodies in infected cells and recombinant pBlueBac viruses are identified on the basis of β-galactosidase expression (Summers, M. D. and Smith, G. E., Texas Agriculture Exp. Station Bulletin No. 1555). Following plaque purification, human calcium channel alpha1G-c expression is measured by the assays described herein.

The cDNA encoding the entire open reading frame for human calcium channel alpha1G-c is inserted into the BamHI site of pBlueBacII. Constructs in the positive orientation are identified by sequence analysis and used to transfect Sf9 cells in the presence of linear AcNPV mild type DNA.

Authentic, active human calcium channel alpha1G-c is found in the cytoplasm of infected cells. Active human calcium channel alpha1G-c is extracted from infected cells by hypotonic or detergent lysis.

EXAMPLE 10

Cloning Human Calcium Channel Alpha1G-c cDNA into a Yeast Expression Vector

Recombinant human calcium channel alpha1G-c is produced in the yeast *S. cerevisiae* following insertion of the optimal human calcium channel alpha1G-c cDNA cistron into expression vectors designed to direct the intracellular or extracellular expression of heterologous proteins. In the case of intracellular expression, vectors such as EmBLyex4 or the like are ligated to the human calcium channel alpha1G-c cistron [Rinas, U. et al., Biotechnology 8: 543–545 (1990); Horowitz B. et al., J. Biol. Chem. 265: 4189–4192 (1989)]. For extracellular expression, the human calcium channel alpha1G-c cistron is ligated into yeast expression vectors which fuise a secretion signal (a yeast or mammalian peptide) to the $NH_2$ terminus of the human calcium channel alpha1G-c protein [Jacobson, M. A., Gene 85: 511–516 (1989); Riett L. and Bellon N. Biochem. 28: 2941–2949 (1989)].

These vectors include, but are not limited to pAVE1>6, which fuses the human serum albumin signal to the expressed cDNA [Steep 0. Biotechnology 8: 42–46 (1990)], and the vector pL8PL which fuses the human lysozyme signal to the expressed cDNA [Yamamoto, Y., Biochem. 28: 2728–2732)]. In addition, human calcium channel alpha1G-c is expressed in yeast as a fusion protein conjugated to ubiquitin utilizing the vector pVEP [Ecker, D. J., J. Biol. Chem. 264: 7715–7719 (1989), Sabin, E. A., Biotechnology 7: 705–709 (1989), McDonnell D. P., Mol. Cell Biol. 9: 5517–5523 (1989)]. The levels of expressed human calcium channel alpha1G-c are determined by the assays described herein.

EXAMPLE 11
Purification of Recombinant Human Calcium Channel Alpha1G-c

Recombinantly produced human calcium channel alpha1G-c may be purified by antibody affinity chromatography.

Human calcium channel alpha1G-c antibody affinity columns are made by adding the anti-human calcium channel alpha1G-c antibodies to Affigel-10 (Bio-Rad), a gel support that is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) together with appropriate membrane solubilizing agents such as detergents and the cell culture supernatant or cell extract containing solubilized human calcium channel alpha1G-c is slowly passed through the column. The column is then washed with phosphate-buffered saline together with detergents until the optical density (A280) falls to background, then the protein is eluted with 0.23 M glycine-HCl (pH 2.6) together with detergents. The purified human calcium channel alpha1G-c protein is then dialyzed against phosphate buffered saline.

REFERENCES

Ahnert-Hilger, G., Stadtbaeumer, A., Struebing, C., Scheruebl, H., Schultz, G., Riecken, E.-O., and Wiedenmann, B. (1996). g-Aminobutyric acid secretion from pancreatic neuroendocrine cells. *Gastroenterology* 110, 1595–1604.

Amoult, C., Cardullo, R. A., Lemos, J. R., and Flonnan, H. M. (1996). Activation of mouse sperm T-type Ca2+ channels by adhesion to the egg zona pellucida. *Proc. Natl. Acad. Sci. U.S.A.* 93, 13004–13009.

Amoult, C., Lemos, J. R., and Florman, h. M. (1997). Voltage-dependent modulation of T-type calcium channels by protein tyrosine phosphorylation. *Embo J.* 16, 1593–1599.

Avery, R. B., and Johnston, D. (1996). Multiple channel types contribute to the low-voltage-activated calcium current in hippocampal CA3 pyramidal neurons. *J. Neurosci.* 16, 5567–5582.

Black, J. L. Lennon, V. A (1999). Identification and cloning of putative human neuronal voltage-gated calcium channel g-2 and g-3 subunits: neurologic implications Mayo Clin. Proc 74: 357–361.

Burgess, D. L., Jones, J. M., Meisler, M. H., and Noebels, J. L. (1997). Mutation of the Ca2+ channel b subunit gene Cchb4 is associated with ataxia and seizures in the lethargic (1h) mouse. *Cell* (Cambridge, Mass.) 88, 385–392.

Cardenas, C. G., Mar, L. P. D., and Scroggs, R. S. (1995). Variation in serotonergic inhibition of calcium channel currents in four types of rat sensory neurons differentiated by membrane properties. *J. Neurophysiol.* 74, 1870–9.

Coulter, D. A., Huguenard, J. R., and Prince, D. A. (1989). Characterization of ethosuximide reduction of low-threshold calcium current in thalamic neurons. *Ann. Neurol.* 25, 582–93.

Coulter, D. A., Huguenard, J. R., and Prince, D. A. (1989). Specific petit mal anticonvulsants reduce calcium currents in thalamic neurons. *Neurosci. Lett.* 98, 74–8.

Dascal, N. (1987). The use of Xenopus oocytes for the study of ion channels. CRC *Critical Reviews in Biochemistry.* 22: 317–387.

Doughty, J. M., Miller, A. L., and Langton, P. D. (1998). Non-specificity of chloride channel blockers in rat cerebral arteries: block of the L-type calcium channel. *J. Physiol.* (Cambridge, U. K.) 507, 433–439.

Enyeart, J. J., Milinar, B., and Enyeart, J. A. (1993). T-type calcium channels are required for adrenocorticotropin-stimulated cortisol production by bovine adrenal zona fasciculata cells. *Mol. Endocrinol.* 7, 1031–40.

Ertel, S. I., Ertel, E. A., and Clozel, J.-P. (1997). T-type Ca2+ channels and pharmacological blockade: potential pathophysiological relevance. In *Cardiovasc. Drugs Ther.*, pp. 723–739.

Formenti, A., Arrigoni, E., and Mancia, M. (1993). Two distinct modulatory effects on calcium channels in adult rat sensory neurons. *Biophys. J.* 64, 1029–37.

Fraser, S. P., Moon, C., and Djamgoz, M. B. A. (1993). Electrophysiology of Xenopus oocytes: An expression system in molecular neurobiology. In: *Electrophysiology.* Wallis, D, ed. IRL, Oxford, UK, pp. 65–86.

Furukawa, T., Nukada, T., Mori, Y., Wakamori, M., Fujita, Y., Ishida, H., Fukuda, K., Kato, S., and Yoshii, M. (1998). Differential interactions of the C terminus and the cytoplasmic I-II loop of neuronal Ca2+ channels with G-protein a and bg subunits. I. Molecular determination. *J. Biol. Chem.* 273, 17585–17594.

Griswold, M. D. (1988). Protein secretions of Sertoli cells. In *Int. Rev. Cytol.*, pp. 133–56.

Hamill, O P, Marty, A, Neher, E, Sakmann, B, and Sigworth, F J (1981). Improved patch-clamp techniques for high-resolution current recording from cells and cell-free membrane patches. *Pflugers Archives* 391: 85–100.

Heine, M., and Wicher, D. (1998). Ca2+ resting current and Ca2+-induced Ca2+ release in insect neurosecretory neurons. *NeuroReport* 9, 3309–3314.

Huguenard, J. R. (1996). Low-threshold calcium currents in central nervous system neurons. In *Annu. Rev. Physiol.*, pp. 329–48.

Iles, D. E.; Lehmann-Hom, F.; Scherer, S. W.; Tsui, L. C.; Olde Weghuis, D.; Suijkerbuijk, R. F.; Heytens, L.; Mikala, G.; Schwartz, A.; et al. (1994). Localization of the gene encoding the α2/δ-subunits of the L-type voltage-dependent calcium channel to chromosome 7q and analysis of the segregation of flanking markers in malignant hyperthermia susceptible families. Hum. Mol. Genet. 3(6), 969–75.

Katz, A. M. (1999). T-type calcium channels may provide a unique target for cardiovascular therapy. *Eur. Heart J. Suppl.* 1, H18–H23.

Kirkup, A. J., Edwards, G., and Weston, A. H. (1996). Investigation of the effects of 5-nitro-2-(3-phenylpropylamino)-benzoic acid (NPPB) on membrane currents in rat portal vein. *Br. J. Pharmacol.* 117, 175–83.

Klugbauer, N., Marais, E., Lacinova, L., and Hofrnann, F. (1999). A T-type calcium channel from mouse brain. *Pfluegers Arch.* 437, 710–715.

Kostyuk, P. G., Molokanova, E. A., Pronchuk, N. F., Savchenko, A. N., and Verkhratsky, A. N. (1992). Different action of ethosuximide on low- and high-threshold threshold calcium currents in rat sensory neurons. *Neuroscience* (Oxford) 51, 755–8.

Lalevee, N., Pluciennik, F., and Joffre, M. (1997). Voltage-dependent calcium current with properties of T-type current in Sertoli cells from immature rat testis in primary cultures. *Biol. Reprod.* 56, 680–687.

Lambert, R. C., Maulet, Y., Mouton, J., Beattie, R., Volsen, S., De Waard, M., and Feltz, A. (1997). T-type Ca2+ current properties are not modified by Ca2+ channel b subunit depletion in nodosus ganglion neurons. *J. Neurosci.* 17, 6621–6628.

Letts, V. A., Felix, R., Biddlecome, G. H., Arikkath, J., Mahaffey, C. L., Valenzuela, A., Bartlett, F. S. II, Mori, Y., Campbell, K. P. and Frankel, W. N. (1998) The mouse stargazer gene encodes a neuronal Ca2+-channel g subunit. Nat. Genet. 19:340.

Leuranguer, V., Bourinet, E., Lory, P., and Nargeot, J. (1998). Antisense depletion of b-subunits fails to affect T-type calcium channels properties in a neuroblastoma cell line. *Neuropharmacology* 37, 701–708.

Lijnen, P., and Petrov, V. (1999). Proliferation of human peripheral blood mononuclear cells during calcium entry blockade. Role of protein Kinase C. Methods Find. *Exp. Clin. Pharmacol.* 21, 253–259.

Liman, Emily R., Tytgat, Jan, Hess, Peter. (1992) Subunit stoichiometry of a mammalian potassium channel determined by construction of multimeric cDNAs. *Neuron* 9: 861–871.

McCormick, D. A., and Bal, T. (1997). Sleep and arousal: thalamocortical mechanisms. *Annu. Rev. Neurosci.* 20, 185–215.

Miller, R. J. (1987). Multiple calcium channels and neuronal function. In *Science* (Washington, D.C., 1883-), pp. 46–52.

Perez-Reyes, E. (1998). Molecular characterization of a novel family of low voltage-activated, T-type, calcium channels. In *J. Bioenerg. Biomembr., pp.* 313–318.

Perez-Reyes, E., Cribbs, L. L., Daud, A., Lacerda, A. E., Barclay, J., Williamson, M. P., Fox, M., Rees, M., and Lee, J.-H. (1998). Molecular characterization of a neuronal low-voltage-activated T-type calcium channel. *Nature* (London) 391, 896–900.

Perez-Reyes, E., and Schneider, T. (1995). Molecular biology of calcium channels. In *Kidney Int.,* pp. 1111–24.

Randall, A. D., and Tsien, R. W. (1997). Contrasting biophysical and pharmacological properties of T-type and R-type calcium channels. *Neuropharmacology* 36, 879–893.

Richard, S., and Nargeot, J. (1998). T-type calcium currents in vascular smooth muscle cells: a role in cellular proliferation? In Low-Voltage-Act. T-type Calcium Channels, Proc. Int. *Electrophysiol. Meet.,* pp. 123–132.

Rousseau, M. F., Hayashida, W., Van Eyll, C., Hess, O. M., Benedict, C. R., Ahn, S., Chapelle, F., Kobrin, I., and Pouleur, H. (1996). Hemodynamic and cardiac effects of the selective T-type and L-type calcium channel blocking agent mibefradil in patients with varying degrees of left ventricular systolic dysfunction. *J. Am. Coll. Cardiol.* 28, 972–979.

Sen, L., and Smith, T. W. (1994). T-type Ca2+ channels are abnormal in genetically determined cardiomyopathic hamster hearts. *Circ. Res.* 75, 149–55.

Sherwin, A. L. (1989). Ethosuximide. Clinical use. In *Antienileotic drugs* (Levy, R., Matteson, R., Meldrum, Penny J K, Dreifuss F E, eds), pp.685–689. New York: Raven.

Stea, A., Dubel, S. J. and Snutch, T. P. (1999). a1B N-type calcium channel isoforms with distinct biophysical properties. *Ann. N.Y. Acad. Sci.* 868: 118–130.

Talley, E. M., Cribbs, L. L., Lee, J.-H., Daud, A., Perez-Reyes, E., and Bayliss, D. A. (1999). Differential distribution of three members of a gene family encoding low voltage-activated (T-type) calcium channels. *J. Neurosci.* 19, 1895–1911.

Todorovic, S. M., and Lingle, C. J. (1998). Pharmacological properties of T-type Ca2+ current in adult rat sensory neurons: effects of anticonvulsant and anesthetic agents. *J. Neurophysiol.* 79, 240–252.

Tsakiridou, E., Bertollini, L., de Curtis, M., Avanzini, G., and Pape, H. C. (1995). Selective increase in T-type calcium conductance of reticular thalamic neurons in a rat model of absence epilepsy. *J. Neurosci.* 15, 3110–17.

Wang, Z., Estacion, M., and Mordan, L. J. (1993). Calcium influx via T-type channels modulates PDGF-induced replication of mouse fibroblasts. *Am. J. Physiol.* 265, C1239–C1246.

Williams, M., Stauderman, K., Harpold, M., Hans, M., Urrutia, A., and Washburn, M. S. Low-voltage activated calcium channel proteins and cDNAs encoding them and the development of calcium channel blockers. In PCT Int. Appl. (Wo: (SibiaNeurosciences, Inc., USA).), pp. 171; WO 9928342.

Williams, M. E., Feldman, D. H., McCue, A. F., Brenner, R., Velicelebi, G., Ellis, S. B., and Harpold, M. M. (1992). Structure and functional expression of a1, a2, and b subunits of a novel human neuronal calcium channel subtype. *Neuron* 8, 71–84.

Williams, M. E., Washburn, M. S., Hans, M., Urrutia, A., Brust, P. F., Prodanovich, P., Harpold, M. M., and Stauderman, K. A. (1999). Structure and functional characterization of a novel human low-voltage activated calcium channel. *J. Neurochem.* 72, 791–799.

Wilson, D., Morimoto, K., Tsuda, Y., and Brown, A. (1983). Interaction between calcium ions and surface charge as it relates to calcium currents. *J. Membr Biol* 72, 117–130.

Xu, X., and Best, P. M. (1990). Increase in T-type calcium current in atrial myocytes from adult rats with growth hormone-secreting tumors. *Proc. Natl. Acad. Sci. U.S.A.* 87, 4655–9.

Zamponi, G. W., Bourinet, E., and Snutch, T. P. (1996). Nickel block of a family of neuronal calcium channels: subtype- and subunit-dependent action at multiple sites. *J. Membr. Biol.* 151, 77–90.

SEQUENCE LISTING

```
<160> NUMBER OF SEQ ID NOS: 5

<210> SEQ ID NO 1
<211> LENGTH: 20
<212> TYPE: DNA
<213> ORGANISM: ARTIFICIAL SEQUENCE
<220> FEATURE:
<223> OTHER INFORMATION: DESCRIPTION OF ARTIFICIAL SEQUENCE: PCR PRIMER
      FOR PROBE
```

<400> SEQUENCE: 1

```
gcactgccag tggccgaggg                                                  20
```

<210> SEQ ID NO 2
<211> LENGTH: 20
<212> TYPE: DNA
<213> ORGANISM: ARTIFICIAL SEQUENCE
<220> FEATURE:
<223> OTHER INFORMATION: DESCRIPTION OF ARTIFICIAL SEQUENCE: PCR PRIMER
      FOR PROBE

<400> SEQUENCE: 2

```
ccatggcgat ggtgatgcag                                                  20
```

<210> SEQ ID NO 3
<211> LENGTH: 6822
<212> TYPE: DNA
<213> ORGANISM: HOMO SAPIENS

<400> SEQUENCE: 3

```
atggacgagg aggaggatgg agcgggcgcc gaggagtcgg gacagccccg gagcttcatg      60
cggctcaacg acctgtcggg ggccggggc cggccggggc cggggtcagc agaaaaggac     120
ccgggcagcg cggactccga ggcggagggg ctgccgtacc cggcgctggc cccggtggtt    180
ttcttctact tgagccagga cagccgcccg cggagctggt gtctccgcac ggtctgtaac    240
ccctggtttg agcgcatcag catgttggtc atccttctca actgcgtgac cctgggcatg    300
ttccggccat gcgaggacat cgcctgtgac tcccagcgct gccggatcct gcaggccttt    360
gatgacttca tctttgcctt ctttgccgtg gagatggtgg tgaagatggt ggccttgggc    420
atctttggga aaagtgttta cctgggagac acttggaacc ggcttgactt tttcatcgtc    480
atcgcaggga tgctggagta ctcgctggac ctgcagaacg tcagcttctc agctgtcagg    540
acagtccgtg tgctgcgacc gctcaggcc attaaccggg tgcccagcat gcgcatcctt    600
gtcacgttgc tgctggatac gctgcccatg ctgggcaacg tcctgctgct ctgcttcttc    660
gtcttcttca tcttcggcat cgtcggcgtc cagctgtggg cagggctgct tcggaaccga    720
tgcttcctac tgagaatttt cagcctcccc ctgagcgtgg aactggagcg ctattaccag    780
acagagaacg aggatgagag ccccttcatc tgctccagc cacgcgagaa cggcatgcgg    840
tcctgcagaa gcgtgcccac gctgcgcggg gacggggcg gtgcccacc ttgcggtctg     900
gactatgagg cctacaacag ctccagcaac accacctgtg tcaactggaa ccagtactac    960
accaactgct cagcggggga gcacaacccc ttcaagggcg ccatcaactt tgacaacatt   1020
ggctatgcct ggatcgccat cttccaggtc atcacgctgg agggctgggt cgacatcatg   1080
tactttgtga tggatgctca ttccttctac aatttcatct acttcatcct cctcatcatc   1140
gtgggctcct tcttcatgat caacctgtgc ctggtggtga ttgccacgca gttctcagag   1200
accaagcagc gggaaagcca gctgatgcgg gagcagcgtg tgcggttcct gtccaacgcc   1260
agcaccctgg ctagcttctc tgagcccggc agctgctatg aggagctgct caagtacctg   1320
gtgtacatcc ttcgtaaggc agcccgcagg ctggctcagg tctctcgggc agcaggtgtg   1380
cgggttgggc tgctcagcag cccagcaccc ctcggggcc aggagaccca gcccagcagc   1440
agctgctctc gctcccaccg ccgcctatcc gtccaccacc tggtgcacca ccaccaccac   1500
catcaccacc actaccacct gggcaatggg acgtcaggg ccccccgggc cagcccggag   1560
atccaggaca gggatgccaa tgggtcccgc aggctcatgc tgccaccacc ctcgacgcct   1620
```

```
gccctctccg gggcccccccc tggtggcgca gagtctgtgc acagcttcta ccatgccgac   1680
tgccacttag agccagtccg ctgccaggcg cccctccca ggtccccatc tgaggcatcc    1740
ggcaggactg tgggcagcgg gaaggtgtat cccaccgtgc acaccagccc tccaccggag   1800
acgctgaagg agaaggcact agtagaggtg gctgccagct ctgggccccc aaccctcacc   1860
agcctcaaca tcccacccgg gccctacagc tccatgcaca agctgctgga cacacagagt   1920
acaggtgcct gccaaagctc ttgcaagatc tccagccctt gcttgaaagc agacagtgga   1980
gcctgtggtc cagacagctg cccctactgt gcccgggccg gggcagggga ggtggagctc   2040
gccgaccgtg aaatgcctga ctcagacagc gaggcagttt atgagttcac acaggatgcc   2100
cagcacagcg acctccggga ccccacagc cggcggcaac ggagcctggg cccagatgca    2160
gagcccagct ctgtgctggc cttctggagg ctaatctgtg acaccttccg aaagattgtg   2220
gacagcaagt actttggccg gggaatcatg atcgccatcc tggtcaacac actcagcatg   2280
ggcatcgaat accacgagca gcccgaggag cttaccaacg ccctagaaat cagcaacatc   2340
gtcttcacca gcctctttgc cctggagatg ctgctgaagc tgcttgtgta tggtcccttt   2400
ggctacatca agaatcccta caacatcttc gatggtgtca ttgtggtcat cagcgtgtgg   2460
gagatcgtgg gccagcaggg gggcggcctg tcggtgctgc ggaccttccg cctgatgcgt   2520
gtgctgaagc tggtgcgctt cctgccggcg ctgcagcggc agctggtggt gctcatgaag   2580
accatggaca acgtggccac cttctgcatg ctgcttatgc tcttcatctt catcttcagc   2640
atcctgggca tgcatctctt cggctgcaag tttgcctctg agcgggatgg ggacaccctg   2700
ccagaccgga agaattttga ctccttgctc tgggccatcg tcactgtctt tcagatcctg   2760
acccaggagg actggaacaa agtcctctac aatggtatgg cctccacgtc gtcctgggcg   2820
gcccttatt tcattgccct catgaccttc ggcaactacg tgctcttcaa tttgctggtc    2880
gccattctgg tggagggctt ccaggcggag gaaatcagca acgggaaga tgcgagtgga    2940
cagttaagct gtattcagct gcctgtcgac tcccagggg gagatgccaa caagtccgaa    3000
tcagagcccg atttcttctc acccagcctg gatggtgatg gggacaggaa gaagtgcttg   3060
gccttggtgt ccctgggaga gcacccggag ctgcggaaga gctgctgcc gcctctcatc    3120
atccacacgg ccgccacacc catgtcgctg ccaagagca ccagcacggg cctgggcgag    3180
gcgctgggcc ctgcgtcgcg ccgcaccagc agcagcgggt cggcagagcc tggggcggcc   3240
cacgagatga agtcaccgcc cagcgcccgc agctctccgc acagccctg gagcgctgca    3300
agcagctgga ccagcaggcg ctccagccgg aacagcctcg gccgtgcacc cagcctgaag   3360
cggagaagcc caagtggaga gcggcggtcc ctgttgtcgg gagaaggcca ggagagccag   3420
gatgaagagg agagctcaga agaggagcgg gccagccctg cgggcagtga ccatcgccac   3480
aggggtccc tggagcggga ggccaagagt tcctttgacc tgccagacac actgcaggtg    3540
ccagggctgc atcgcactgc cagtggccga gggtctgctt ctgagcacca ggactgcaat   3600
ggcaagtcgc cttcagggcg cctggcccgg ccctgcggc tgatgacccc ccactggat    3660
ggggatgacg ccgatgacga gggcaacctg agcaaggggg aacgggtccg cgcgtggatc   3720
cgagcccgac tccctgcctg ctgcctcgag cgagactcct ggtcagccta catcttccct   3780
cctcagtcca ggttccgcct cctgtgtcac cggatcatca cccacaagat gttcgaccac   3840
gtggtccttg tcatcatctt ccttaactgc atcaccatcg ccatggagcg ccccaaaatt   3900
gacccccaca gcgctgaacg catcttcctg accctctcca attacatctt caccgcagtc   3960
```

-continued

| | | | | |
|---|---|---|---|---|
| tttctggctg | aaatgacagt | gaaggtggtg | gcactgggct | ggtgcttcgg | ggagcaggcg | 4020 |
| tacctgcgga | gcagttggaa | cgtgctggac | gggctgttgg | tgctcatctc | cgtcatcgac | 4080 |
| attctggtgt | ccatggtctc | tgacagcggc | accaagatcc | tgggcatgct | gagggtgctg | 4140 |
| cggctgctgc | ggaccctgcg | cccgctcagg | gtgatcagcc | gggcgcaggg | gctgaagctg | 4200 |
| gtggtggaga | cgctgatgtc | ctcactgaaa | cccatcggca | acattgtagt | catctgctgt | 4260 |
| gccttcttca | tcattttcgg | catcttgggg | gtgcagctct | tcaaagggaa | gttttttcgtg | 4320 |
| tgccagggcg | aggataccag | gaacatcacc | aataaatcgg | actgtgccga | ggccagttac | 4380 |
| cggtgggtcc | ggcacaagta | caactttgac | aaccttggcc | aggccctgat | gtccctgttc | 4440 |
| gttttggcct | ccaaggatgg | ttgggtggac | atcatgtacg | atgggctgga | tgctgtgggc | 4500 |
| gtggaccagc | agcccatcat | gaaccacaac | ccctggatgc | tgctgtactt | catctcgttc | 4560 |
| ctgctcattg | tggccttctt | tgtcctgaac | atgtttgtgg | gtgtggtggt | ggagaacttc | 4620 |
| cacaagtgtc | ggcagcacca | ggaggaagag | gaggcccggc | ggcgggagga | gaagcgccta | 4680 |
| cgaagactgg | agaaaaagag | aaggagtaag | gagaagcaga | tggctgaagc | ccagtgcaaa | 4740 |
| ccttactact | ccgactactc | ccgcttccgg | ctcctcgtcc | accacttgtg | caccagccac | 4800 |
| tacctggacc | tcttcatcac | aggtgtcatc | gggctgaacg | tggtcaccat | ggccatggag | 4860 |
| cactaccagc | agccccagat | tctggatgag | gctctgaaga | tctgcaacta | catcttcact | 4920 |
| gtcatctttg | tcttggagtc | agttttcaaa | cttgtggcct | ttggtttccg | tcggttcttc | 4980 |
| caggacaggt | ggaaccagct | ggacctggcc | attgtgctgc | tgtccatcat | gggcatcacg | 5040 |
| ctggaggaaa | tcgaggtcaa | cgcctcgctg | cccatcaacc | ccaccatcat | ccgcatcatg | 5100 |
| agggtgctgc | gcattgcccg | agtgctgaag | ctgctgaaga | tggctgtggg | catgcgggcg | 5160 |
| ctgctggaca | cggtgatgca | ggccctgccc | caggtgggga | acctgggact | tctcttcatg | 5220 |
| ttgttgtttt | tcatctttgc | agctctgggc | gtggagctct | tggagacct | ggagtgtgac | 5280 |
| gagacacacc | cctgtgaggg | cctgggccgt | catgccacct | tcggaacttt | ggcatggcc | 5340 |
| ttcctaaccc | tcttccgagt | ctccacaggt | gacaattgga | atggcattat | gaaggacacc | 5400 |
| ctccgggact | gtgaccagga | gtccacctgc | tacaacacgg | tcatctcgcc | tatctacttt | 5460 |
| gtgtccttcg | tgctgacggc | ccagttcgtg | ctagtcaacg | tggtgatcgc | cgtgctgatg | 5520 |
| aagcacctgg | aggagagcaa | caaggaggcc | aaggaggagg | ccgagctaga | ggctgagctg | 5580 |
| gagctggaga | tgaagaccct | cagccccag | ccccactcgc | cactgggcag | cccttcctc | 5640 |
| tggcctgggg | tcgagggccc | cgacagcccc | gacagcccca | agcctggggc | tctgcaccca | 5700 |
| gcggcccacg | cgagatcagc | ctcccactt | tccctggagc | accccacgat | gcagccccac | 5760 |
| cccacggagc | tgccaggacc | agacttactg | actgtgcgga | agtctggggt | cagccgaacg | 5820 |
| cactctctgc | ccaatgacag | ctacatgtgt | cggcatggga | gcactgccga | ggggcccctg | 5880 |
| ggacacaggg | gctgggggct | ccccaaagct | cagtcaggct | ccgtcttgtc | cgttcactcc | 5940 |
| cagccagcag | ataccagcta | catcctgcag | cttcccaaag | atgcacctca | tctgctccag | 6000 |
| ccccacagcg | ccccaacctg | gggcaccatc | cccaaactgc | ccccaccagg | acgctcccct | 6060 |
| ttggctcaga | ggccactcag | gcgccaggca | gcaataagga | ctgactcctt | ggacgttcag | 6120 |
| ggtctgggca | gccgggaaga | cctgctggca | gaggtgagtg | ggccctcccc | gcccctggcc | 6180 |
| cgggcctact | ctttctgggg | ccagtcaagt | acccaggcac | agcagcactc | ccgcagccac | 6240 |
| agcaagatct | ccaagcacat | gaccccgcca | gcccttgcc | caggcccaga | acccaactgg | 6300 |
| ggcaagggcc | ctccagagac | cagaagcagc | ttagagttgg | acacggagct | gagctggatt | 6360 |

```
tcaggagacc tcctgccccc tggcggccag gaggagcccc catccccacg ggacctgaag    6420
aagtgctaca cgcgtggaggc ccagagctgc cagcgccggc ctacgtcctg gctggatgag    6480
cagaggagac actctatcgc cgtcagctgc ctggacagcg gctcccaacc ccacctgggc    6540
acagacccct ctaaccttgg gggccagcct cttgggggc ccgggagccg cccaagaaa      6600 aaactcagcc cgcctagtat caccatagac ccccccgaga gccaaggtcc tcggaccccg    6660
cccagccctg gtatctgcct ccggaggagg gctccgtcca gcgactccaa ggatcccttg    6720
gcctctggcc cccctgacag catggctgcc tcgccctccc caaagaaaga tgtgctgagt    6780
ctctccggtt tatcctctga cccagcagac ctggacccct ga                       6822
```

<210> SEQ ID NO 4
<211> LENGTH: 7741
<212> TYPE: DNA
<213> ORGANISM: HOMO SAPIENS

<400> SEQUENCE: 4

```
ccgggtcgac ccacgcgtcc ggatccctcc tcccctcccc cgccgcctgg cgcggagccg      60
ggacgatgct gacccttag atccggctcc agctgcgccg cgggaagagg gggcgcccct     120
ccccggaccc ccgccctccg ccgctgcccc ccttttcgtt cgccctctcg gggcggcttc    180
gccgaaggta gcgccgaatc cggcaaccgg agcctgggcg cgaagcgaag aagccggaac    240
aaagtgaggg ggagccggcc ggctggcccg ggaagcccca ggggcgcagg ggaagcggga    300
ctcgcgccgg gcggggtttc cctgcgcccc ggcgccccgc gggcagcatg cccctgcggg    360 caggggggagc tgggctgaac tggccctccc gggggctcag cttgcgccct agagcccacc    420
agatgtgccc ccgccggggc cccgggttg cgtgaggaca cctcctctga ggggcgccgc     480
ttgcccctct ccggatcgcc cggggccccg gctggccaga ggatggacga ggaggaggat    540
ggagcgggcg ccgaggagtc gggacagccc cggagcttca tgcggctcaa cgacctgtcg    600
ggggccgggg gccggccggg gccggggtca gcagaaaagg accgggcag cgcggactcc     660 gaggcggagg ggctgccgta cccggcgctg gccccggtgg ttttcttcta cttgagccag    720
gacagccgcc cgcggagctg gtgtctccgc acggtctgta accctggtt tgagcgcatc     780 agcatgttgg tcatccttct caactgcgtg acctgggca tgttccggcc atgcgaggac     840
atcgcctgtg actcccagcg ctgccggatc ctgcaggcct tgatgactt catctttgcc     900 ttctttgccg tggagatggt ggtgaagatg gtggccttgg gcatctttgg gaaaaagtgt    960
tacctgggag acacttggaa ccggcttgac ttttttcatcg tcatcgcagg gatgctggag    1020
tactcgctgg acctgcagaa cgtcagcttc tcagctgtca ggacagtccg tgtgctgcga    1080
ccgctcaggg ccattaaccg ggtgcccagc atgcgcatcc ttgtcacgtt gctgctggat    1140
acgctgccca tgctgggcaa cgtcctgctg ctctgcttct tcgtcttctt catcttcggc    1200
atcgtcggcg tccagctgtg ggcagggctg cttcggaacc gatgcttcct acctgagaat    1260
ttcagcctcc ccctgagcgt ggacctggag cgctattacc agacagagaa cgaggatgag    1320
agccccttca tctgctccca gccacgcgag aacggcatgc ggtcctgcag aagcgtgccc    1380
acgctgcgcg gggacggggg cggtggccca ccttgcggtc tggactatga ggcctacaac    1440
agctccagca acaccaccctg tgtcaactgg aaccagtact acaccaactg ctcagcgggg    1500
gagcacaacc cctcaaaggg cgccatcaac tttgacaaca ttggctatgc ctggatcgcc    1560
atcttccagg tcatcacgct ggagggctgg gtcgacatca tgtactttgt gatggatgct    1620
```

-continued

```
cattccttct acaatttcat ctacttcatc ctcctcatca tcgtgggctc cttcttcatg    1680
atcaacctgt gcctggtggt gattgccacg cagttctcag agaccaagca gcgggaaagc    1740
cagctgatgc gggagcagcg tgtgcggttc ctgtccaacg ccagcaccct ggctagcttc    1800
tctgagcccg gcagctgcta tgaggagctg ctcaagtacc tggtgtacat ccttcgtaag    1860
gcagcccgca ggctggctca ggtctctcgg gcagcaggtg tgcgggttgg gctgctcagc    1920
agcccagcac ccctcggggg ccaggagacc cagcccagca gcagctgctc tcgctcccac    1980
cgccgcctat ccgtccacca cctggtgcac caccaccacc accatcacca ccactaccac    2040
ctgggcaatg ggacgctcag ggccccccgg gccagcccgg agatccagga cagggatgcc    2100
aatgggtccc gcaggctcat gctgccacca ccctcgacgc ctgccctctc cggggccccc    2160
cctggtggcg cagagtctgt gcacagcttc taccatgccg actgccactt agagccagtc    2220
cgctgccagg cgccccctcc caggtcccca tctgaggcat ccggcaggac tgtgggcagc    2280
gggaaggtgt atcccaccgt gcacaccagc cctccaccgg agacgctgaa ggagaaggca    2340
ctagtagagg tggctgccag ctctgggccc ccaacccctca ccagcctcaa catcccaccc    2400
gggccctaca gctccatgca caagctgctg agacacagga gtacaggtgc ctgccaaagc    2460
tcttgcaaga tctccagccc ttgcttgaaa gcagacagtg gagcctgtgg tccagacagc    2520
tgcccctact gtgcccgggc cggggcaggg gaggtggagc tcgccgaccg tgaaatgcct    2580
gactcagaca gcgaggcagt ttatgagttc acacaggatg cccagcacag cgacctccgg    2640 gaccccccaca gccggcggca acggagcctg ggccagatg cagagcccag ctctgtgctg    2700
gccttctgga ggctaatctg tgacaccttc cgaaagattg tggacagcaa gtactttggc    2760
cggggaatca tgatcgccat cctggtcaac acactcagca tgggcatcga ataccacgag    2820
cagcccgagg agcttaccaa cgccctagaa atcagcaaca tcgtcttcac cagcctcttt    2880
gccctggaga tgctgctgaa gctgcttgtg tatggtccct ttggctacat caagaatccc    2940
tacaacatct tcgatggtgt cattgtggtc atcagcgtgt gggagatcgt gggccagcag    3000
gggggcggcc tgtcggtgct gcggaccttc cgcctgatgc gtgtgctgaa gctggtgcgc    3060
ttcctgccgg cgctgcagcg gcagctggtg gtgctcatga agaccatgga caacgtggcc    3120
accttctgca tgctgcttat gctcttcatc ttcatcttca gcatcctggg catgcatctc    3180
ttcggctgca gtttgcctc tgagcgggat ggggacaccc tgccagaccg gaagaatttt    3240
gactccttgc tctgggccat cgtcactgtc tttcagatcc tgacccagga ggactggaac    3300
aaagtcctct acaatggtat ggcctccacg tcgtcctggg cggcccttta tttcattgcc    3360
ctcatgacct tcggcaacta cgtgctcttc aatttgctgg tcgccattct ggtggagggc    3420
ttccaggcgg aggaaatcag caaacgggaa gatgcgagtg acagttaag ctgtattcag    3480 ctgcctgtcg actcccaggg gggagatgcc aacaagtccg aatcagagcc cgatttcttc    3540
tcacccagcc tggatggtga tggggacagg aagaagtgct tggccttggt gtccctggga    3600
gagcacccgg agctgcggaa gagcctgctg ccgcctctca tcatccacac ggccgccaca    3660
cccatgtcgc tgcccaagag caccagcacg ggcctgggcg aggcgctggg ccctgcgtcg    3720
cgccgcacca gcagcagcgg gtcggcagag cctgggggcgg cccacgagat gaagtcaccg    3780
cccagcgccc gcagctctcc gcacagcccc tggagcgctg caagcagctg gaccagcagg    3840
cgctccagcc ggaacagcct cggccgtgca cccagcctga gcggagaag cccaagtgga    3900 gagcggcggt ccctgttgtc gggagaaggc caggagagcc aggatgaaga ggagagctca    3960
gaagaggagc gggccagccc tgcgggcagt gaccatcgcc acagggggtc cctggagcgg    4020
```

```
gaggccaaga gttcctttga cctgccagac acactgcagg tgccagggct gcatcgcact      4080
gccagtggcc gagggtctgc ttctgagcac caggactgca atggcaagtc ggcttcaggg      4140
cgcctggccc gggccctgcg gcctgatgac cccccactgg atggggatga cgccgatgac      4200
gagggcaacc tgagcaaagg ggaacgggtc cgcgcgtgga tccgagcccg actccctgcc      4260
tgctgcctcg agcgagactc ctggtcagcc tacatcttcc ctcctcagtc caggttccgc      4320
ctcctgtgtc accggatcat cacccacaag atgttcgacc acgtggtcct tgtcatcatc      4380
ttccttaact gcatcaccat cgccatggag cgccccaaaa ttgaccccca cagcgctgaa      4440
cgcatcttcc tgaccctctc caattacatc ttcaccgcag tctttctggc tgaaatgaca      4500
gtgaaggtgg tggcactggg ctggtgcttc ggggagcagg cgtacctgcg gagcagttgg      4560
aacgtgctgg acgggctgtt ggtgctcatc tccgtcatcg acattctggt gtccatggtc      4620
tctgacagcg gcaccaagat cctgggcatg ctgagggtgc tgcggctgct gcggaccctg      4680
cgcccgctca gggtgatcag ccgggcgcag gggctgaagc tggtggtgga cgctgatg      4740 tcctcactga aacccatcgg caacattgta gtcatctgct gtgccttctt catcatttc      4800 ggcatcttgg gggtgcagct cttcaaaggg aagttttcg tgtgccaggg cgaggatacc      4860
aggaacatca ccaataaatc ggactgtgcc gaggccagtt accggtgggt ccggcacaag      4920
tacaactttg acaaccttgg ccaggccctg atgtccctgt tcgttttggc ctccaaggat      4980
ggttgggtgg acatcatgta cgatgggctg atgctgtgg gcgtggacca gcagcccatc      5040
atgaaccaca accctggat gctgctgtac ttcatctcgt tcctgctcat tgtggccttc      5100
tttgtcctga acatgtttgt gggtgtggtg gtggagaact tccacaagtg tcggcagcac      5160
caggaggaag aggaggcccg gcggcgggag gagaagcgcc tacgaagact ggagaaaaag      5220
agaaggagta aggagaagca gatggctgaa gcccagtgca aaccttacta ctccgactac      5280
tcccgcttcc ggctcctcgt ccaccacttg tgcaccagcc actacctgga cctcttcatc      5340
acaggtgtca tcgggctgaa cgtggtcacc atggccatgg agcactacca gcagcccag      5400 attctggatg aggctctgaa gatctgcaac tacatcttca ctgtcatctt tgtcttggag      5460
tcagttttca aacttgtggc cttttggttc cgtcggttct tccaggacag gtggaaccag      5520
ctggacctgg ccattgtgct gctgtccatc atgggcatca cgctggagga aatcgaggtc      5580
aacgcctcgc tgcccatcaa ccccaccatc atccgcatca tgagggtgct gcgcattgcc      5640
cgagtgctga agctgctgaa gatggctgtg gcatgcggg cgctgctgga cacggtgatg      5700
caggccctgc cccaggtggg gaacctggga cttctcttca tgttgttgtt tttcatcttt      5760
gcagctctgg gcgtggagct cttttgagac ctggagtgtg acgagacaca ccctgtgag      5820 ggcctgggcc gtcatgccac ctttcggaac tttggcatgg ccttcctaac cctcttccga      5880
gtctccacag gtgacaattg gaatggcatt atgaaggaca ccctccggga ctgtgaccag      5940
gagtccacct gctacaacac ggtcatctcg cctatctact ttgtgtcctt cgtgctgacg      6000
gcccagttcg tgctagtcaa cgtggtgatc gccgtgctga tgaagcacct ggaggagagc      6060
aacaaggagg ccaaggagga ggccgagcta gaggctgagc tggagctgga tgaagacc      6120 ctcagccccc agccccactc gccactgggc agcccttcc tctggcctgg ggtcgagggc      6180
cccgacagcc ccgacagccc caagcctggg gctctgcacc cagcggccca cgcgagatca      6240
gcctcccact tttcctgga gcaccccacg atgcagcccc accccacgga gctgccagga      6300
ccagacttac tgactgtgcg gaagtctggg gtcagccgaa cgcactctct gcccaatgac      6360
```

```
agctacatgt gtcggcatgg gagcactgcc gaggggcccc tgggacacag gggctggggg    6420
ctccccaaag ctcagtcagg ctccgtcttg tccgttcact cccagccagc agataccagc    6480
tacatcctgc agcttcccaa agatgcacct catctgctcc agcccacag cgccccaacc    6540 tggggcacca tccccaaact gcccccacca ggacgctccc ctttggctca gaggccactc    6600
aggcgccagg cagcaataag gactgactcc ttggacgttc agggtctggg cagccgggaa    6660
gacctgctgg cagaggtgag tgggccctcc cgcccctgg cccgggccta ctctttctgg     6720
ggccagtcaa gtacccaggc acagcagcac tcccgcagcc acagcaagat ctccaagcac    6780 atgacccgc cagccccttg cccaggccca gaacccaact ggggcaaggg ccctccagag     6840
accagaagca gcttagagtt ggacacggag ctgagctgga tttcaggaga cctcctgccc    6900
cctggcggcc aggaggagcc cccatcccca cgggacctga agaagtgcta cagcgtggag    6960
gcccagagct gccagcgccg gcctacgtcc tggctggatg agcagaggag acactctatc    7020
gccgtcagct gcctggacag cggctcccaa ccccacctgg gcacagaccc ctctaacctt    7080
gggggccagc tcttgggggg gcccgggagc cggcccaaga aaaaactcag cccgcctagt    7140
atcaccatag accccccga gagccaaggt cctcggaccc cgcccagccc tggtatctgc     7200
ctccggagga gggctccgtc cagcgactcc aaggatccct tggcctctgg ccccctgac     7260 agcatggctg cctcgccctc cccaaagaaa gatgtgctga gtctctccgg tttatcctct    7320
gacccagcag acctggaccc ctgagtcctg ccccactttc ccactcacct ttctccactg    7380
ggtgccaagt cctagctcct cctcctgggc tatattcctg acaaaagttc catatagaca    7440
ccaaggaggc ggaggcgctc ctccctgcct cagtggctct gggtacctgc aagcagaact    7500
tccaaagaga gttaaaagca gcagcccgg caactctggc tccaggcaga aggagaggcc     7560
cggtgcagct gaggttcccg acaccagaag ctgttgggag aaagcaatac gtttgtgcag    7620
aatctctatg tatattctat tttattaaat taattgaatc tagtatatgc gggatgtacg    7680 acatttgtg actgaagaga cttgtttcct tctacttta tgtgtctcag aatattttg      7740 a                                                                   7741
```

<210> SEQ ID NO 5
<211> LENGTH: 2273
<212> TYPE: PRT
<213> ORGANISM: HOMO SAPIENS

<400> SEQUENCE: 5

```
MET ASP GLU GLU ASP GLY ALA GLY ALA GLU GLU SER GLY GLN PRO
 1               5                  10                  15

ARG SER PHE MET ARG LEU ASN ASP LEU SER GLY ALA GLY GLY ARG PRO
                20                  25                  30

GLY PRO GLY SER ALA GLU LYS ASP PRO GLY SER ALA ASP SER GLU ALA
            35                  40                  45

GLU GLY LEU PRO TYR PRO ALA LEU ALA PRO VAL VAL PHE PHE TYR LEU
        50                  55                  60

SER GLN ASP SER ARG PRO ARG SER TRP CYS LEU ARG THR VAL CYS ASN
65                  70                  75                  80

PRO TRP PHE GLU ARG ILE SER MET LEU VAL ILE LEU LEU ASN CYS VAL
                85                  90                  95

THR LEU GLY MET PHE ARG PRO CYS GLU ASP ILE ALA CYS ASP SER GLN
                100                 105                 110

ARG CYS ARG ILE LEU GLN ALA PHE ASP ASP PHE ILE PHE ALA PHE PHE
            115                 120                 125
```

-continued

```
ALA VAL GLU MET VAL VAL LYS MET VAL ALA LEU GLY ILE PHE GLY LYS
    130                 135                 140
LYS CYS TYR LEU GLY ASP THR TRP ASN ARG LEU ASP PHE PHE ILE VAL
145                 150                 155                 160
ILE ALA GLY MET LEU GLU TYR SER LEU ASP LEU GLN ASN VAL SER PHE
                165                 170                 175
SER ALA VAL ARG THR VAL ARG VAL LEU ARG PRO LEU ARG ALA ILE ASN
                180                 185                 190
ARG VAL PRO SER MET ARG ILE LEU VAL THR LEU LEU LEU ASP THR LEU
            195                 200                 205
PRO MET LEU GLY ASN VAL LEU LEU LEU CYS PHE PHE VAL PHE ILE
    210                 215                 220
PHE GLY ILE VAL GLY VAL GLN LEU TRP ALA GLY LEU LEU ARG ASN ARG
225                 230                 235                 240
CYS PHE LEU PRO GLU ASN PHE SER LEU PRO LEU SER VAL ASP LEU GLU
                245                 250                 255
ARG TYR TYR GLN THR GLU ASN GLU ASP GLU SER PRO PHE ILE CYS SER
                260                 265                 270
GLN PRO ARG GLU ASN GLY MET ARG SER CYS ARG SER VAL PRO THR LEU
            275                 280                 285
ARG GLY ASP GLY GLY GLY GLY PRO PRO CYS GLY LEU ASP TYR GLU ALA
    290                 295                 300
TYR ASN SER SER SER ASN THR THR CYS VAL ASN TRP ASN GLN TYR TYR
305                 310                 315                 320
THR ASN CYS SER ALA GLY GLU HIS ASN PRO PHE LYS GLY ALA ILE ASN
                325                 330                 335
PHE ASP ASN ILE GLY TYR ALA TRP ILE ALA ILE PHE GLN VAL ILE THR
                340                 345                 350
LEU GLU GLY TRP VAL ASP ILE MET TYR PHE VAL MET ASP ALA HIS SER
            355                 360                 365
PHE TYR ASN PHE ILE TYR PHE ILE LEU LEU ILE ILE VAL GLY SER PHE
    370                 375                 380
PHE MET ILE ASN LEU CYS LEU VAL VAL ILE ALA THR GLN PHE SER GLU
385                 390                 395                 400
THR LYS GLN ARG GLU SER GLN LEU MET ARG GLU GLN ARG VAL ARG PHE
                405                 410                 415
LEU SER ASN ALA SER THR LEU ALA SER PHE SER GLU PRO GLY SER CYS
                420                 425                 430
TYR GLU GLU LEU LEU LYS TYR LEU VAL TYR ILE LEU ARG LYS ALA ALA
            435                 440                 445
ARG ARG LEU ALA GLN VAL SER ARG ALA ALA GLY VAL ARG VAL GLY LEU
    450                 455                 460
LEU SER SER PRO ALA PRO LEU GLY GLY GLN GLU THR GLN PRO SER SER
465                 470                 475                 480
SER CYS SER ARG SER HIS ARG ARG LEU SER VAL HIS HIS LEU VAL HIS
                485                 490                 495
HIS HIS HIS HIS HIS HIS HIS TYR HIS LEU GLY ASN GLY THR LEU
                500                 505                 510
ARG ALA PRO ARG ALA SER PRO GLU ILE GLN ASP ARG ASP ALA ASN GLY
            515                 520                 525
SER ARG ARG LEU MET LEU PRO PRO PRO SER THR PRO ALA LEU SER GLY
    530                 535                 540
```

-continued

```
ALA PRO PRO GLY GLY ALA GLU SER VAL HIS SER PHE TYR HIS ALA ASP
545             550                 555                 560

CYS HIS LEU GLU PRO VAL ARG CYS GLN ALA PRO PRO ARG SER PRO
                565                 570                 575

SER GLU ALA SER GLY ARG THR VAL GLY SER GLY LYS VAL TYR PRO THR
            580                 585                 590

VAL HIS THR SER PRO PRO GLU THR LEU LYS GLU LYS ALA LEU VAL
        595                 600                 605

GLU VAL ALA ALA SER SER GLY PRO PRO THR LEU THR SER LEU ASN ILE
    610                 615                 620

PRO PRO GLY PRO TYR SER SER MET HIS LYS LEU LEU GLU THR GLN SER
625             630                 635                 640

THR GLY ALA CYS GLN SER SER CYS LYS ILE SER SER PRO CYS LEU LYS
                645                 650                 655

ALA ASP SER GLY ALA CYS GLY PRO ASP SER CYS PRO TYR CYS ALA ARG
                660                 665                 670

ALA GLY ALA GLY GLU VAL GLU LEU ALA ASP ARG GLU MET PRO ASP SER
            675                 680                 685

ASP SER GLU ALA VAL TYR GLU PHE THR GLN ASP ALA GLN HIS SER ASP
            690                 695                 700

LEU ARG ASP PRO HIS SER ARG ARG GLN ARG SER LEU GLY PRO ASP ALA
705             710                 715                 720

GLU PRO SER SER VAL LEU ALA PHE TRP ARG LEU ILE CYS ASP THR PHE
                725                 730                 735

ARG LYS ILE VAL ASP SER LYS TYR PHE GLY ARG GLY ILE MET ILE ALA
                740                 745                 750

ILE LEU VAL ASN THR LEU SER MET GLY ILE GLU TYR HIS GLU GLN PRO
            755                 760                 765

GLU GLU LEU THR ASN ALA LEU GLU ILE SER ASN ILE VAL PHE THR SER
            770                 775                 780

LEU PHE ALA LEU GLU MET LEU LEU LYS LEU LEU VAL TYR GLY PRO PHE
785             790                 795                 800

GLY TYR ILE LYS ASN PRO TYR ASN ILE PHE ASP GLY VAL ILE VAL VAL
                805                 810                 815

ILE SER VAL TRP GLU ILE VAL GLY GLN GLN GLY GLY LEU SER VAL
            820                 825                 830

LEU ARG THR PHE ARG LEU MET ARG VAL LEU LYS LEU VAL ARG PHE LEU
            835                 840                 845

PRO ALA LEU GLN ARG GLN LEU VAL VAL LEU MET LYS THR MET ASP ASN
850             855                 860

VAL ALA THR PHE CYS MET LEU LEU MET LEU PHE ILE PHE ILE PHE SER
865                 870                 875                 880

ILE LEU GLY MET HIS LEU PHE GLY CYS LYS PHE ALA SER GLU ARG ASP
                885                 890                 895

GLY ASP THR LEU PRO ASP ARG LYS ASN PHE ASP SER LEU LEU TRP ALA
            900                 905                 910

ILE VAL THR VAL PHE GLN ILE LEU THR GLN GLU ASP TRP ASN LYS VAL
        915                 920                 925

LEU TYR ASN GLY MET ALA SER THR SER SER TRP ALA ALA LEU TYR PHE
    930                 935                 940

ILE ALA LEU MET THR PHE GLY ASN TYR VAL LEU PHE ASN LEU LEU VAL
945                 950                 955                 960

ALA ILE LEU VAL GLU GLY PHE GLN ALA GLU GLU ILE SER LYS ARG GLU
```

```
                          965                 970                 975
ASP ALA SER GLY GLN LEU SER CYS ILE GLN LEU PRO VAL ASP SER GLN
                980                 985                 990
GLY GLY ASP ALA ASN LYS SER GLU SER GLU PRO ASP PHE PHE SER PRO
        995                 1000                1005
SER LEU ASP GLY ASP GLY ASP ARG LYS LYS CYS LEU ALA LEU VAL SER
    1010                1015                1020
LEU GLY GLU HIS PRO GLU LEU ARG LYS SER LEU LEU PRO PRO LEU ILE
1025                1030                1035                1040
ILE HIS THR ALA ALA THR PRO MET SER LEU PRO LYS SER THR SER THR
                    1045                1050                1055
GLY LEU GLY GLU ALA LEU GLY PRO ALA SER ARG ARG THR SER SER SER
            1060                1065                1070
GLY SER ALA GLU PRO GLY ALA ALA HIS GLU MET LYS SER PRO PRO SER
        1075                1080                1085
ALA ARG SER SER PRO HIS SER PRO TRP SER ALA ALA SER SER TRP THR
    1090                1095                1100
SER ARG ARG SER SER ARG ASN SER LEU GLY ARG ALA PRO SER LEU LYS
1105                1110                1115                1120
ARG ARG SER PRO SER GLY GLU ARG ARG SER LEU LEU SER GLY GLU GLY
                1125                1130                1135
GLN GLN SER GLN ASP GLN GLU GLU SER SER GLU GLU GLU ARG ALA SER
            1140                1145                1150
PRO ALA GLY SER ASP HIS ARG HIS ARG GLY SER LEU GLU ARG GLU ALA
        1155                1160                1165
LYS SER SER PHE ASP LEU PRO ASP THR LEU GLN VAL PRO GLY LEU HIS
    1170                1175                1180
ARG THR ALA SER GLY ARG GLY SER ALA SER GLU HIS GLN ASP CYS ASN
1185                1190                1195                1200
GLY LYS SER ALA SER GLY ARG LEU ALA ARG ALA LEU ARG PRO ASP ASP
                1205                1210                1215
PRO PRO LEU ASP GLY ASP ASP ALA ASP ASP GLU GLY ASN LEU SER LYS
            1220                1225                1230
GLY GLU ARG VAL ARG ALA TRP ILE ARG ALA ARG LEU PRO ALA CYS CYS
        1235                1240                1245
LEU GLU ARG ASP SER TRP SER ALA TYR ILE PHE PRO PRO GLN SER ARG
    1250                1255                1260
PHE ARG LEU LEU CYS HIS ARG ILE ILE THR HIS LYS MET PHE ASP HIS
1265                1270                1275                1280
VAL VAL LEU VAL ILE ILE PHE LEU ASN CYS ILE THR ILE ALA MET GLU
                1285                1290                1295
ARG PRO LYS ILE ASP PRO HIS SER ALA GLU ARG ILE PHE LEU THR LEU
            1300                1305                1310
SER ASN TYR ILE PHE THR ALA VAL PHE LEU ALA GLU MET THR VAL LYS
        1315                1320                1325
VAL VAL ALA LEU GLY TRP CYS PHE GLY GLU GLN ALA TYR LEU ARG SER
    1330                1335                1340
SER TRP ASN VAL LEU ASP GLY LEU LEU VAL LEU ILE SER VAL ILE ASP
1345                1350                1355                1360
ILE LEU VAL SER MET VAL SER ASP SER GLY THR LYS ILE LEU GLY MET
                1365                1370                1375
LEU ARG VAL LEU ARG LEU LEU ARG THR LEU ARG PRO LEU ARG VAL ILE
            1380                1385                1390
```

-continued

```
SER ARG ALA GLN GLY LEU LYS LEU VAL VAL GLU THR LEU MET SER SER
         1395                1400                1405
LEU LYS PRO ILE GLY ASN ILE VAL VAL ILE CYS CYS ALA PHE PHE ILE
    1410                1415                1420
ILE PHE GLY ILE LEU GLY VAL GLN LEU PHE LYS GLY LYS PHE PHE VAL
1425                1430                1435                1440
CYS GLN GLY GLU ASP THR ARG ASN ILE THR ASN LYS SER ASP CYS ALA
             1445                1450                1455
GLU ALA SER TYR ARG TRP VAL ARG HIS LYS TYR ASN PHE ASP ASN LEU
             1460                1465                1470
GLY GLN ALA LEU MET SER LEU PHE VAL LEU ALA SER LYS ASP GLY TRP
         1475                1480                1485
VAL ASP ILE MET TYR ASP GLY LEU ASP ALA VAL GLY VAL ASP GLN GLN
    1490                1495                1500
PRO ILE MET ASN HIS ASN PRO TRP MET LEU LEU TYR PHE ILE SER PHE
1505                1510                1515                1520
LEU LEU ILE VAL ALA PHE PHE VAL LEU ASN MET PHE VAL GLY VAL VAL
             1525                1530                1535
VAL GLU ASN PHE HIS LYS CYS ARG GLN HIS GLN GLU GLU GLU GLU ALA
         1540                1545                1550
ARG ARG ARG GLU GLU LYS ARG LEU ARG ARG LEU GLU LYS LYS ARG ARG
         1555                1560                1565
SER LYS GLU LYS GLN MET ALA GLU ALA GLN CYS LYS PRO TYR TYR SER
    1570                1575                1580
ASP TYR SER ARG PHE ARG LEU LEU VAL HIS HIS LEU CYS THR SER HIS
1585                1590                1595                1600
TYR LEU ASP LEU PHE ILE THR GLY VAL ILE GLY LEU ASN VAL VAL THR
             1605                1610                1615
MET ALA MET GLU HIS TYR GLN GLN PRO GLN ILE LEU ASP GLU ALA LEU
             1620                1625                1630
LYS ILE CYS ASN TYR ILE PHE THR VAL ILE PHE VAL LEU GLU SER VAL
         1635                1640                1645
PHE LYS LEU VAL ALA PHE GLY PHE ARG ARG PHE PHE GLN ASP ARG TRP
         1650                1655                1660
ASN GLN LEU ASP LEU ALA ILE VAL LEU LEU SER ILE MET GLY ILE PRO
1665                1670                1675                1680
LEU GLU GLN ILE GLU VAL ASN ALA SER LEU PRO ILE ASN PRO THR ILE
             1685                1690                1695
ILE ARG ILE MET ARG VAL LEU ARG ILE ALA ARG VAL LEU LYS LEU LEU
             1700                1705                1710
LYS MET ALA VAL GLY MET ARG ALA LEU LEU ASP THR VAL MET GLN ALA
         1715                1720                1725
LEU PRO GLN VAL GLY ASN LEU GLY LEU LEU PHE MET LEU LEU PHE PHE
    1730                1735                1740
ILE PHE ALA ALA LEU GLY VAL GLU LEU PHE GLY ASP LEU GLU CYS ASP
1745                1750                1755                1760
GLU THR HIS PRO CYS GLU GLY LEU GLY ARG HIS ALA THR PHE ARG ASN
             1765                1770                1775
PHE GLY MET ALA PHE LEU THR LEU PHE ARG VAL SER THR GLY ASP ASN
             1780                1785                1790
TRP ASN GLY ILE MET LYS ASP THR LEU ARG ASP CYS ASP GLN GLU SER
         1795                1800                1805
```

```
THR CYS TYR ASN THR VAL ILE SER PRO ILE TYR PHE VAL SER PHE VAL
    1810                1815                1820

LEU THR ALA GLN PHE VAL LEU VAL ASN VAL VAL ILE ALA VAL LEU MET
1825                1830                1835                1840

LYS HIS LEU GLU GLU SER ASN LYS GLU ALA LYS GLU ALA GLU LEU
            1845                1850                1855

GLU ALA GLU LEU GLU LEU GLU MET LYS THR LEU SER PRO GLN PRO HIS
            1860                1865                1870

SER PRO LEU GLY SER PRO PHE LEU TRP PRO GLY VAL GLU GLY PRO ASP
            1875                1880                1885

SER PRO ASP SER PRO LYS PRO GLY ALA LEU HIS PRO ALA ALA HIS ALA
    1890                1895                1900

ARG SER ALA SER HIS PHE SER LEU GLU HIS PRO THR MET GLN PRO HIS
1905                1910                1915                1920

PRO THR GLU LEU PRO GLY PRO ASP LEU LEU THR VAL ARG LYS SER GLY
                1925                1930                1935

VAL SER ARG THR HIS SER LEU PRO ASN ASP SER TYR MET CYS ARG HIS
            1940                1945                1950

GLY SER THR ALA GLU GLY PRO LEU GLY HIS ARG GLY TRP GLY LEU PRO
        1955                1960                1965

LYS ALA GLN SER GLY SER VAL LEU SER VAL HIS SER GLN PRO ALA ASP
    1970                1975                1980

THR SER TYR ILE LEU GLN LEU PRO LYS ASP ALA PRO HIS LEU LEU GLN
1985                1990                1995                2000

PRO HIS SER ALA PRO THR TRP GLY THR ILE PRO LYS LEU PRO PRO PRO
            2005                2010                2015

GLY ARG SER PRO LEU ALA GLN ARG PRO LEU ARG ARG GLN ALA ALA ILE
        2020                2025                2030

ARG THR ASP SER LEU ASP VAL GLN GLY LEU GLY SER ARG GLU ASP LEU
        2035                2040                2045

LEU ALA GLU VAL SER GLY PRO SER PRO PRO LEU ALA ARG ALA TYR SER
    2050                2055                2060

PHE TRP GLY GLN SER SER THR GLN ALA GLN GLN HIS SER ARG SER HIS
2065                2070                2075                2080

SER LYS ILE SER LYS HIS MET THR PRO PRO ALA PRO CYS PRO GLY PRO
            2085                2090                2095

GLU PRO ASN TRP GLY LYS GLY PRO PRO GLU THR ARG SER SER LEU GLU
            2100                2105                2110

LEU ASP THR GLU LEU SER TRP ILE SER GLY ASP LEU LEU PRO PRO GLY
        2115                2120                2125

GLY GLN GLU GLU PRO PRO SER PRO ARG ASP LEU LYS LYS CYS TYR SER
    2130                2135                2140

VAL GLU ALA GLN SER CYS GLN ARG ARG PRO THR SER TRP LEU ASP GLU
2145                2150                2155                2160

GLN ARG ARG HIS SER ILE ALA VAL SER CYS LEU ASP SER GLY SER GLN
            2165                2170                2175

PRO HIS LEU GLY THR ASP PRO SER ASN LEU GLY GLY GLN PRO LEU GLY
        2180                2185                2190

GLY PRO GLY SER ARG PRO LYS LYS LYS LEU SER PRO PRO SER ILE THR
        2195                2200                2205

ILE ASP PRO PRO GLU SER GLN GLY PRO ARG THR PRO PRO SER PRO GLY
    2210                2215                2220

ILE CYS LEU ARG ARG ARG ALA PRO SER SER ASP SER LYS ASP PRO LEU
```

-continued

```
           2225                2230                2235                2240
ALA SER GLY PRO PRO ASP SER MET ALA ALA SER PRO SER PRO LYS LYS
                      2245                2250                2255
ASP VAL LEU SER LEU SER GLY LEU SER SER ASP PRO ALA ASP LEU ASP
            2260                2265                2270
PRO
```

What is claimed is:

1. An isolated and purified DNA molecule that encodes human calcium channel alpha1G-c channel protein, comprising an amino acid sequence set forth in SEQ ID NO: 5.

2. The isolated and purified DNA molecule of claim 1, having a nucleotide sequence selected from a group consisting of SEQ ID NO: 3 and SEQ ID NO: 4.

3. An expression vector for expression of a human calcium channel alpha1G-c channel protein in a recombinant host, wherein said vector contains a recombinant nucleic acid molecule encoding human calcium channel alpha1G-c protein comprising an amino acid sequence set forth in SEQ ID NO: 5.

4. The expression vector of claim 3, wherein the expression vector contains a cloned nucleic acid molecule encoding human calcium channel alpha1G-c channel protein having a nucleotide sequence selected from a group consisting of SEQ ID NO: 3 and SEQ ID NO: 4.

5. A process for expression of human calcium channel alpha1G-c channel protein in a recombinant host cell, comprising:
   (a) transferring the expression vector of claim 3 into suitable host cells; and
   (b) culturing the host cells of step (a) under conditions which allow expression of the human calcium channel alpha1G-c channel protein from the expression vector.

6. A recombinant host cell containing a recombinantly cloned nucleic acid molecule encoding human calcium channel alpha1G-c channel protein comprising an amino acid sequence set forth in SEQ ID NO: 5.

7. The recombinant host cell of claim 6, wherein said nucleic acid molecule has a nucleotide sequence selected from a group consisting of SEQ ID NO: 3 and SEQ ID NO: 4.

* * * * *